United States Patent
Kao et al.

(10) Patent No.: US 11,613,750 B2
(45) Date of Patent: Mar. 28, 2023

(54) METHODS OF REDUCING VIRUS MOLECULE LEVELS

(71) Applicant: Aligos Therapeutics, Inc., South San Francisco, CA (US)

(72) Inventors: Chia-Cheng Kao, Brisbane, CA (US); Lawrence M. Blatt, San Mateo, CA (US); Leonid Beigelman, San Mateo, CA (US)

(73) Assignee: Aligos Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 17/091,293

(22) Filed: Nov. 6, 2020

(65) Prior Publication Data

US 2021/0230591 A1 Jul. 29, 2021

Related U.S. Application Data

(60) Provisional application No. 62/931,962, filed on Nov. 7, 2019.

(51) Int. Cl.
*C07H 21/02* (2006.01)
*C07H 21/04* (2006.01)
*C12N 15/113* (2010.01)

(52) U.S. Cl.
CPC ........ *C12N 15/113* (2013.01); *C12N 2310/11* (2013.01); *C12N 2310/14* (2013.01)

(58) Field of Classification Search
CPC .......................... C12N 15/113; C12N 2310/14
See application file for complete search history.

(56) References Cited

FOREIGN PATENT DOCUMENTS

| CN | 110393791 A | 11/2019 |
|---|---|---|
| WO | WO 2009/080852 A1 | 7/2009 |
| WO | WO 2016/142948 A1 | 9/2016 |
| WO | WO 2018/026812 A1 | 2/2018 |

OTHER PUBLICATIONS

Campos et al. (Journal of Virology, 2017, 91, 4, e01706-16, 1-17).*
Allerson et al. (J. Med. Chem. 2005, 48, 901-904).*
Huang, K.L. et al. 2009 Involvement of GRP78 in inhibition of HBV secretion by Boehmeria nivea extract in human HepG2 2.2.15 cells. Journal of Viral Hepatitis, 2009, 16:367-375.
Spurgers, K.F. et al. 2010 Identification of essential filovirion-associated host factors by serial proteomic analysis and RNAi screen. Molecular and Cellular Proteomics, 2010, 9:2690-2703.
PCT Written Opinion of the International Searching Authority dated Feb. 9, 2021 for Application No. PCT/US2020/059385.
Alarcon C.R. et al. 2015. HNRNPA2B1 is a mediator of m6A-dependent nuclear RNA processing events. Cell 162: 1299-308.
Aznarez, I., et al. 2018. Mechanism of nonsense-mediated mRNA decay stimulation by splicing factor SRSF1. Cell Report 23: 2186-98.
Ballesta, J.P., Remacha, M. 1996. The large ribosomal stalk as a regulatory element of the eukaryotic translational machinery. Prog. Nucleic Acid Res. Mol Biol. 55: 157-193.
Campos, R.K. et al. 2017. RPLP1 and RPLP2 are essential flavivirus host factors that promote early viral accumulation. J. Virol. 91: e01706-16.
Campos R.K. et al., 2019. Ribosomal stalk proteins RPLP1 and RPLP2 promote biogenesis of flaviviral and cellular multi-pass transmembrane proteins. BioRxiv. Doi 10.110/713016.
Choi. A.K.H. et al. 2015. Structures of eukaryotic ribosomal stalk proteins and their complex with trichosanthin and their implications in recruiting ribosome-inactivating proteins to the ribosomes. Toxins 7: 638.
Coronaviridae Study Group of the International Committee on Taxonomy of Viruses. 2020. The species of Severe acute respiratory syndrome-related coronavirus: classifying the 2019-nCoV and naming it SARS-CoV2. Nature Microbiology 5, 536-544.
Imam H. et al. 2018. N6-methyladenosine modification of the Hepatitis B virus RNA differentially regulates the viral life cycle., Proc. Natl. Acad. Sci. USA 115: 8829-34.
Kibbe WA. 2007 OligoCalc: an online oligonucleotide properties calculator. Nucl. Acids Res. 35 (webserver issue): May 25.
Ko C, Park W.J., Park S, Kim S, Windisch, M.P. and Ryu, W.S. 2015. The FDA approved drug irbesartan inhibits HBV infection in HepG2 cells stably expressing sodium taurocholate co-transporting polypeptide. Antivir. Ther. 20: 835-42.
Li, W. 2015. The hepatitis B virus receptor. Annu. Rev. Cell Dev. Biol. 31: 125-47.
Li, Y. et al., 2019. Hepatitis B surface antigen activates unfolded protein response in forming ground glass hepatocytes of chronic hepatitis B. Viruses 11: 386.
Liang, T.J. 2009. Hepatitis B: The virus and disease. Hepatology 49: S13-S21.
Mitra, B., Thapa, R. J., Guo H., and Block, T.M. 2018. Host functions used by hepatitis B virus to complete its life cycle: implications for developing host-targeting agents to treat chronic hepatitis B. Antiviral Res. 158: 185-98.
Pollack, J. and Ganem D. 1993. An RNA stem-loop structure directs hepatitis B virus genomic RNA encapsidation. J. Virol. 67: 3254-63.
Shin, H.J., Kim, S.S., Cho, Y. H., Lee, S.G. and Rho, H.M. 2002. Host cell proteins binding to the encapsidation signal episilon in the hepatitis B virus RNA. Arch. Virol. 147: 471-91.
Wang, M. et al. 2009. Role of the unfolded protein response regulator GRP78/BiP in development, cancer and neurological disorders. Antioxid. & Redox Signal. 11: 2307.
Wang, L., Wen, M., and Cao X. 2019. Nuclear HNRNPA2B1 initiates and amplifies the innate immune response to DNA viruses. Science: eaav0758.

(Continued)

*Primary Examiner* — Amy H Bowman
(74) *Attorney, Agent, or Firm* — Knobbe, Martens, Olson & Bear, LLP

(57) ABSTRACT

Methods of reducing levels of virus molecules and/or treating viral infections include contacting cells with an oligonucleotide inhibitor that targets a cellular host factor that is a target RNA or target protein involved in viral replication. A pharmaceutical composition can include such an oligonucleotide inhibitor in an amount effective for treating an infection, such as a hepatitis B infection or a respiratory virus infection, such as a coronavirus infection.

16 Claims, 7 Drawing Sheets

Specification includes a Sequence Listing.

(56) References Cited

OTHER PUBLICATIONS

Wang M. Cao R., Zhang L., Yang X., Liu J. et al. 2020. Remdesivir and chloroquine effectively inhibits the recently emerged novel coronavirus (2019-nCoV) in vitro. Cell Research 30, 269-271.
Warfield K.L. 2019. Lack of selective resistance of influenza A virus in presence of targeted antiviral UV-4B. Scientific Report. 9:7484.
Zhao R. et al. 2011. Hepatoma cell line HepG2.2.15 demonstrate distinct biological features compared with parental HepG2. World J. Gastroenterol. 17(9):1152-1159.

* cited by examiner

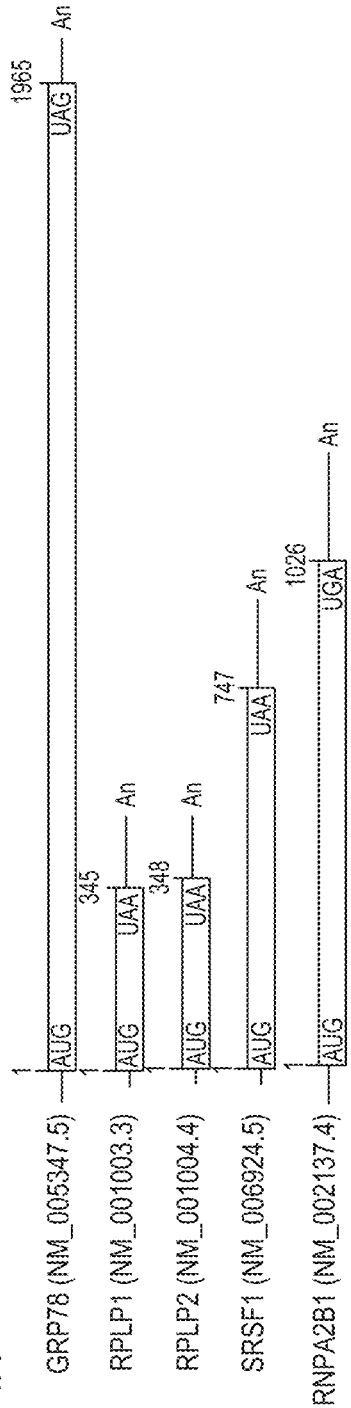

FIG. 1A

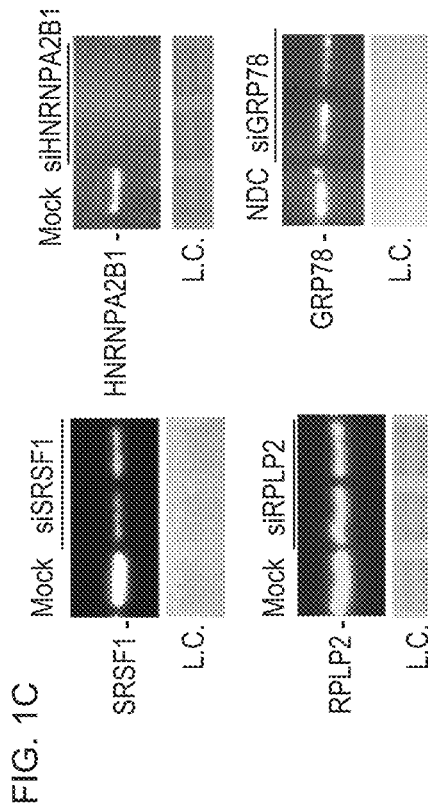

FIG. 1. siRNAs targeting cellular RNAs can reduce the level of HBsAg made by HepG2.2.15 cells. A) Schematic for five target mRNAs illustrating the nucleobase numbering. The NCBI accession number denotes the game variant for the target. The protein-coding open reading frame is denoted as a rectangle and the first adenylate of the initiation codon is designated nucleotide 1. The second number represents the last nucleotide of the termination codon. "An" represents the polyA tail. B) Summary of siRNA knockdowns on cell viability and HBsAg levels. Cell viability was assessed by ATP levels determined using the CellTiter-Glow reagent and the data normalized to the level in mock-treated cells. HBsAg levels was quantified using ELISA and the data normalized to the level in the mock-treated cells. C) Sample Western blots images showing that the siRNAs reduce teh levels of the cellular protein that they are designed to target. The blots were probed with antisera specific to the target. L.C. denotes a loading control.

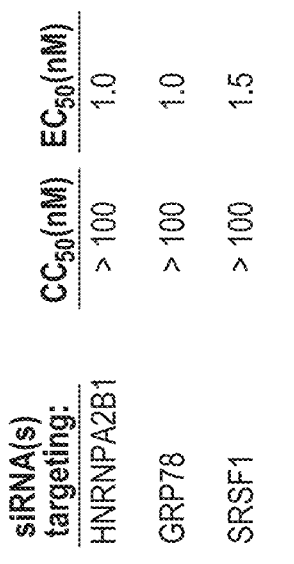
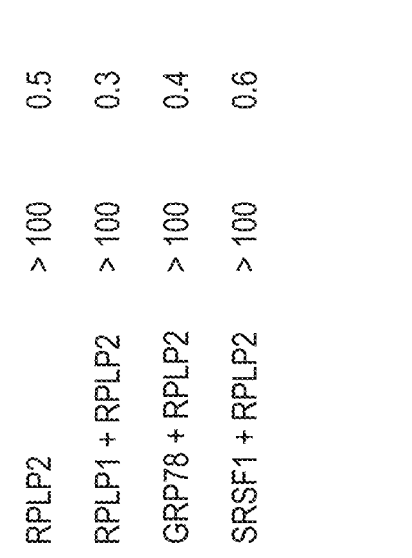
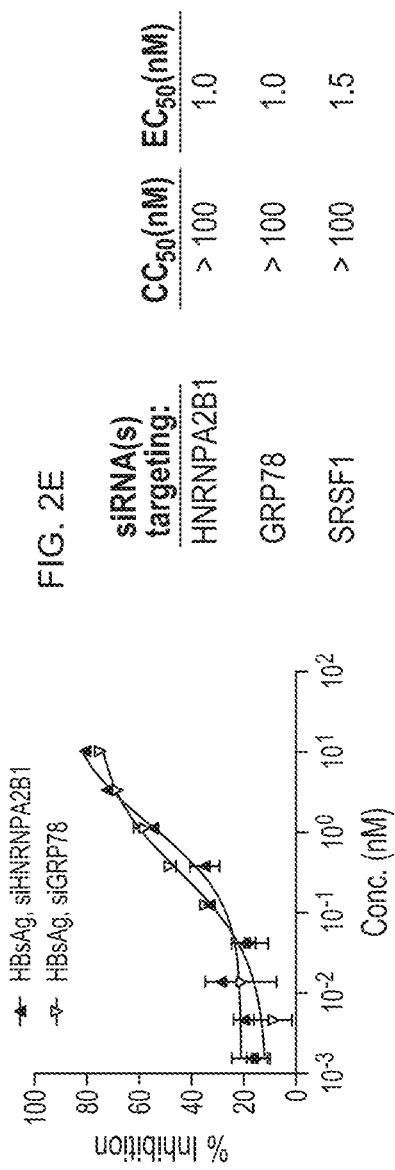
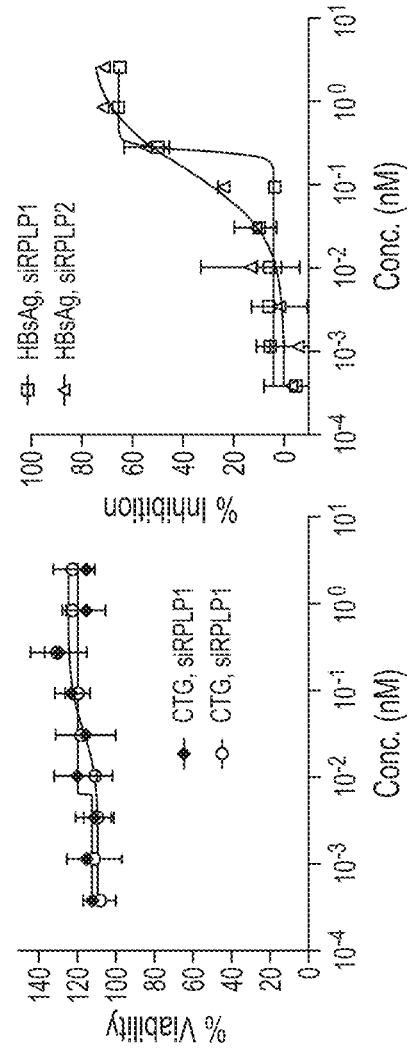
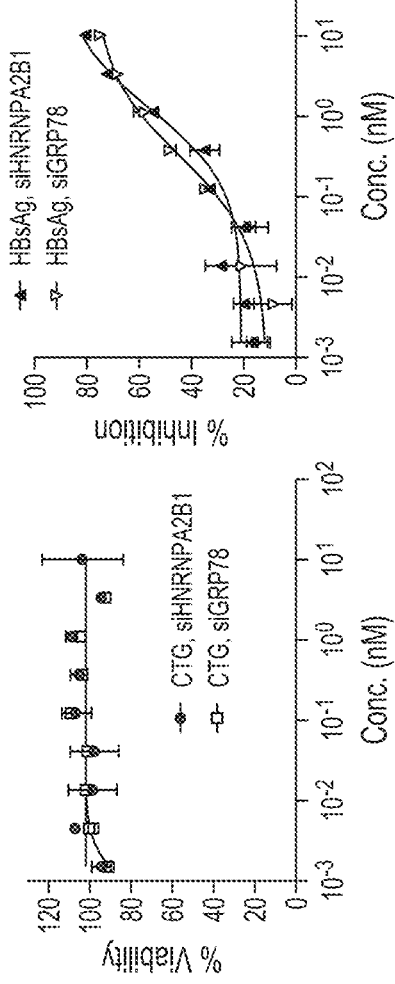

FIG. 2E

| siRNA(s) targeting: | CC$_{50}$(nM) | EC$_{50}$(nM) |
|---|---|---|
| HNRNPA2B1 | > 100 | 1.0 |
| GRP78 | > 100 | 1.0 |
| SRSF1 | > 100 | 1.5 |
| RPLP1 | > 100 | 0.9 |
| RPLP2 | > 100 | 0.5 |
| RPLP1 + RPLP2 | > 100 | 0.3 |
| GRP78 + RPLP2 | > 100 | 0.4 |
| SRSF1 + RPLP2 | > 100 | 0.6 |

FIG. 2. siRNAs targeting cellular factors can reduce HBV S antigen levels in HepG2.2.15 cells. A and C) Sample analyses of the cytotoxicity (CC$_{50}$) of the siRNAs that can knock down cellular factors in HepG2.2.15 cells. B and D) Sample analyses of the effective concentrations (EC$_{50}$) of the siRNAs that can reduce HBsAg levels to 50% of the mock-treated samples E) Summary of the CC$_{50}$ and EC$_{50}$ values of siRNAs that can target either single or combinations of the cellular factors.

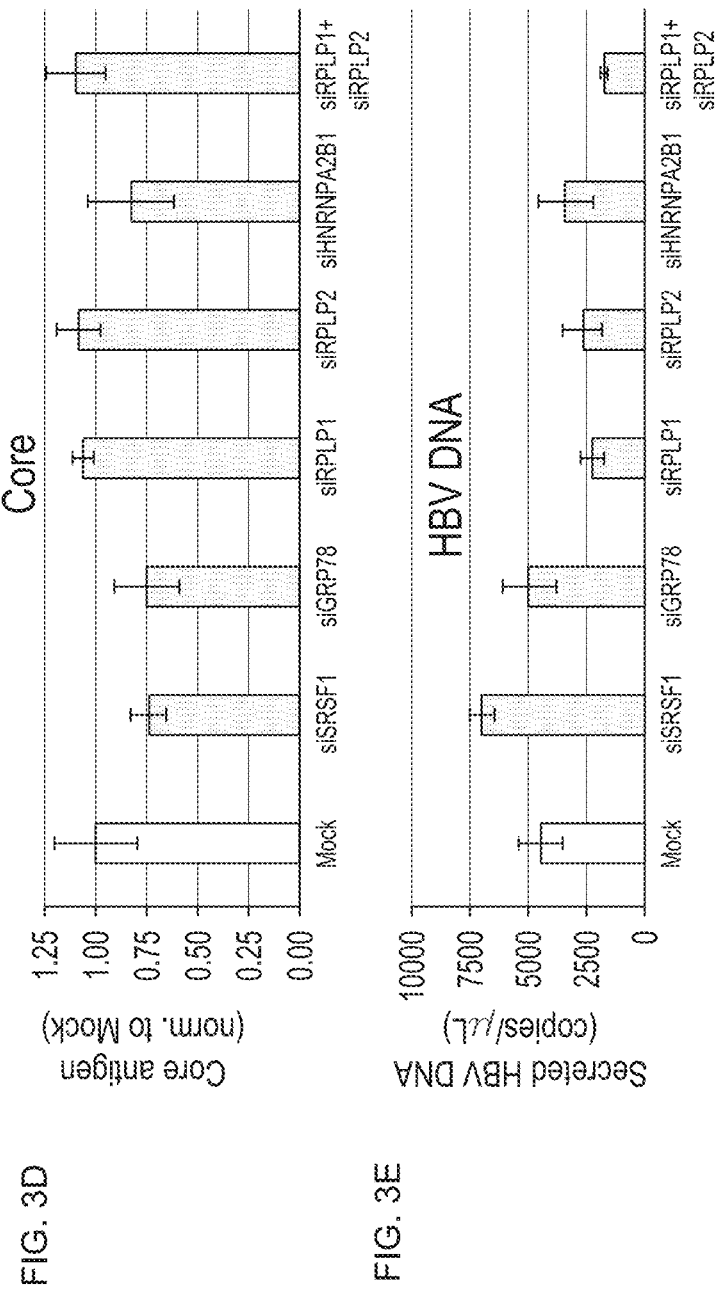

FIG. 3. siRNA targeting host factors can reduce the levels of multiple HBV molecules in HepG2.2.15 cells. All siRNAs were introduced into cells at a final concentration of 10 nM, except for cells treated with both siRNA to RPLP1 and RPLP2, that were treated with a final concentrations of 5nM of each set of siRNA. A) Quantification of the effects on cell viability. All data were normalized to the amount of protein produced by mock-treated cells. B-D) Quantification of the HBV proteins made by HepG2.2. 15 cells after treatment with siRNAs. HBsAg and HBeAg in the cell culture media were assessed using ELISAs. E) Quantification of the amounts of HBV DNAs found in the cell culture media. The copy number of the DNAs were determined using qPCR.

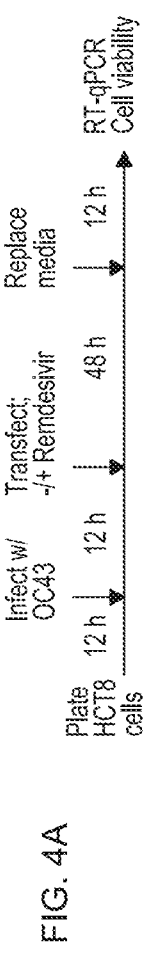
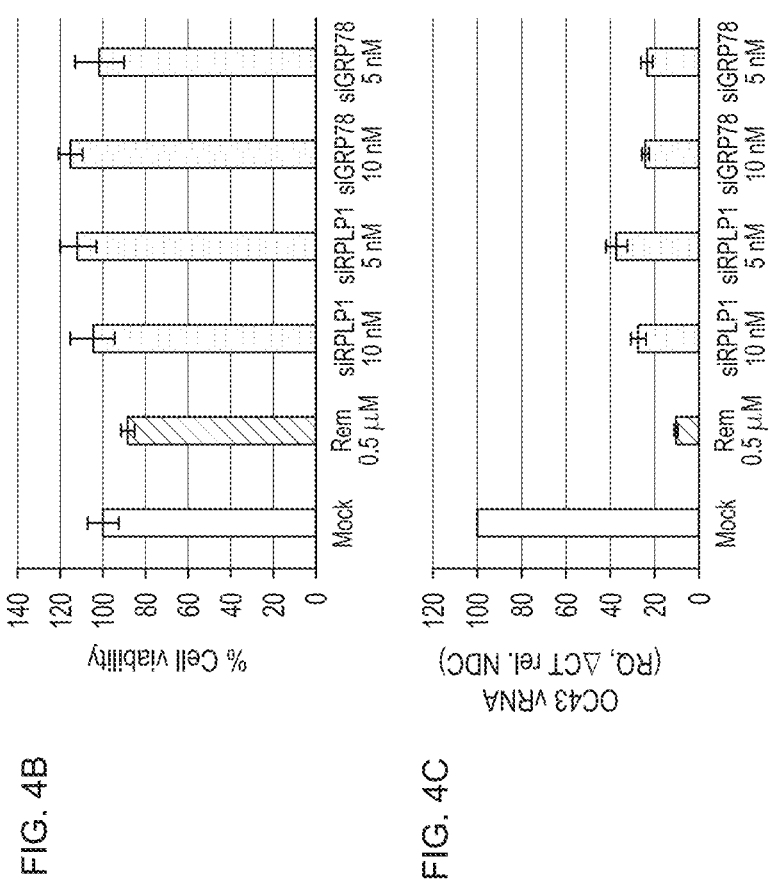

FIG. 4. siRNAs that target host factors can inhibit Coronavirus OC43 infection. A) Schematic of the experiment. B) Effects of the experiment on cell viability, as determined by The CellTiter Glow assay. All data were normalized to the signal in the mock-treated cells. C) Quantification of the amounts of OC43 virion RNA in the cell culture media. The virion RNAs were quantified using qPCR with Coronavirus-specific primers and the signal normalized to the mock-treated controls. Remdesivir (REM) is a nucleotide prodrug known to inhibit Coronavirus replication.

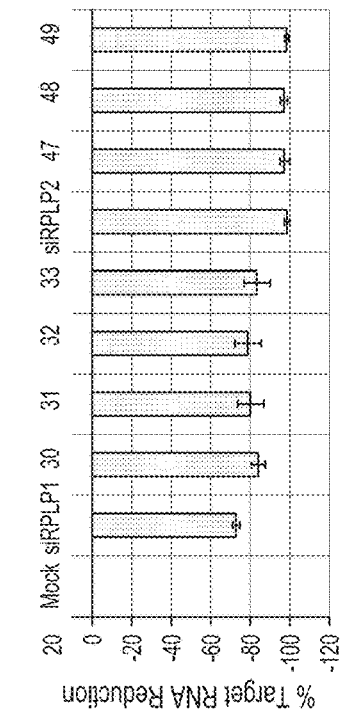
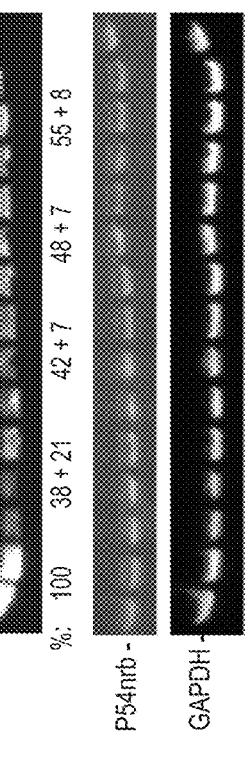
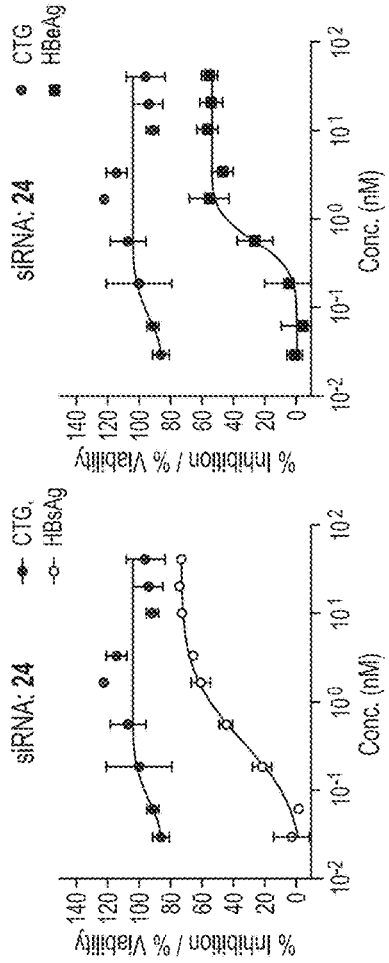
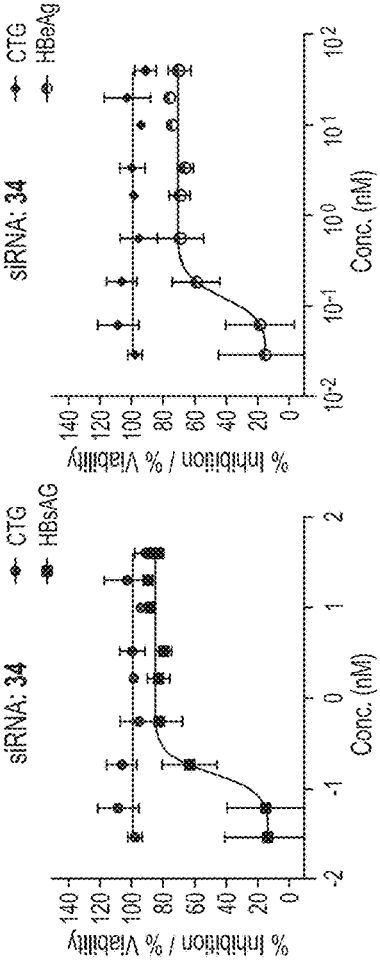

FIG. 5. Activities of the siRNAs targeting RPLP1 and RPLP2. A) Dose responses and cytotoxicity profiles of siRNAs in inhibiting HBsAg and HBeAg levels. HBsAg and HBeAg were quantified using ELISAs and Cytotoxicity was determined using the CellTiter-Glo reagent. All data were normalized to the mock-treated controls in the same experiment. siRNA 24 targets RPLP1 and RPLP2-34 targets RPLP2. B) Knockdown of RPLP1 and RPLP2 RNAs by a sampling of siRNAs transfected into cells at a concentration of 10 nM. The reduction of the target RNA was assessed using qPCR and calculated using the ΔCt value. C) Knockdown of RPLP1 and RPLP2 by a sampling of siRNAs transfected into cells at 10 nM. The cellular proteins were detected using Western blots probed with specific antibodies. P54nrb and GAPDH serve as loading controls.

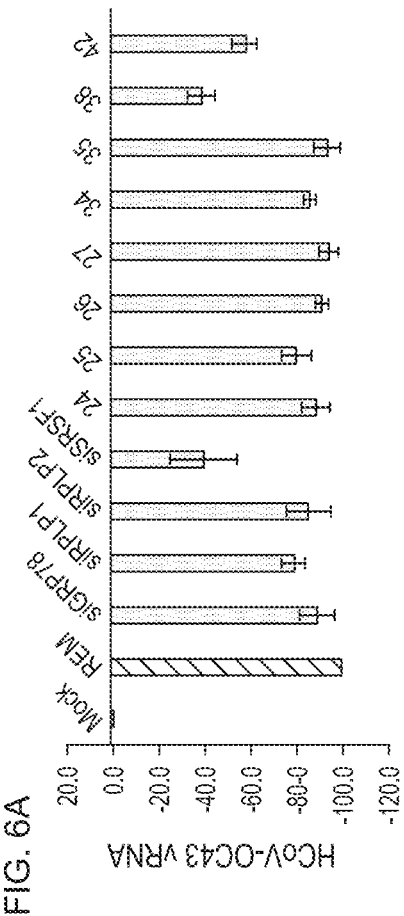
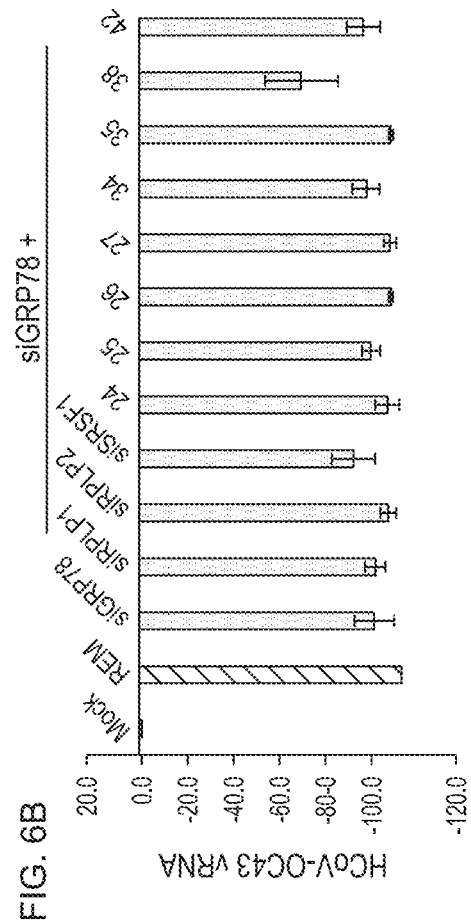
FIG. 6. Host factor siRNAs can decrease human coronavirus OC43 virion production. A) Reduction in OC43 virion RNAs by

SEQUENCE LISTING

```
<160> NUMBER OF SEQ ID NOS: 52

<210> SEQ ID NO 1
<211> LENGTH: 21
<212> TYPE: RNA
<213> ORGANISM: Artificial Sequence
<220> FEATURE:
<223> OTHER INFORMATION: Homo sapiens

<400> SEQUENCE: 1
aagcgcauug auacuagaaa u                                                    21

<210> SEQ ID NO 2
<211> LENGTH: 21
<212> TYPE: RNA
<213> ORGANISM: Artificial Sequence
<220> FEATURE:
<223> OTHER INFORMATION: Homo sapiens

<400> SEQUENCE: 2
aggaaccauc ccguggcaua a                                                    21

<210> SEQ ID NO 3
<211> LENGTH: 21
<212> TYPE: RNA
<213> ORGANISM: Artificial Sequence
<220> FEATURE:
<223> OTHER INFORMATION: Homo sapiens

<400> SEQUENCE: 3
aagaaagaag guuacccaug c                                                    21

<210> SEQ ID NO 4
<211> LENGTH: 21
<212> TYPE: RNA
<213> ORGANISM: Artificial Sequence
<220> FEATURE:
<223> OTHER INFORMATION: Homo sapiens

<400> SEQUENCE: 4
aaagaugaag cuguagcgua u                                                    21

<210> SEQ ID NO 5
<211> LENGTH: 21
<212> TYPE: RNA
<213> ORGANISM: Artificial Sequence
<220> FEATURE:
<223> OTHER INFORMATION: Homo sapiens
```

<400> SEQUENCE: 5
aacgguggaa auuucggacc a                                                  21

<210> SEQ ID NO 6
<211> LENGTH: 21
<212> TYPE: RNA
<213> ORGANISM: Artificial Sequence
<220> FEATURE:
<223> OTHER INFORMATION: Homo sapiens

<400> SEQUENCE: 6
aagcuguuug uuggcggaau u                                                  21

<210> SEQ ID NO 7
<211> LENGTH: 21
<212> TYPE: RNA
<213> ORGANISM: Artificial Sequence
<220> FEATURE:
<223> OTHER INFORMATION: Homo sapiens

<400> SEQUENCE: 7
aaggagagua guugagccaa a                                                  21

<210> SEQ ID NO 8
<211> LENGTH: 21
<212> TYPE: RNA
<213> ORGANISM: Artificial Sequence
<220> FEATURE:
<223> OTHER INFORMATION: Homo sapiens

<400> SEQUENCE: 8
aagaggagga ucugauggau a                                                  21

<210> SEQ ID NO 9
<211> LENGTH: 21
<212> TYPE: RNA
<213> ORGANISM: Artificial Sequence
<220> FEATURE:
<223> OTHER INFORMATION: Homo sapiens

<400> SEQUENCE: 9
aaugacaugg gcuuuggucu u                                                  21

<210> SEQ ID NO 10
<211> LENGTH: 21
<212> TYPE: RNA
<213> ORGANISM: Artificial Sequence
<220> FEATURE:
<223> OTHER INFORMATION: Homo sapiens

<400> SEQUENCE: 10
aaaagaagaa uccgaggagu c                                                  21

<210> SEQ ID NO 11
<211> LENGTH: 21
<212> TYPE: RNA
<213> ORGANISM: Artificial Sequence
<220> FEATURE:
<223> OTHER INFORMATION: Homo sapiens

<400> SEQUENCE: 11
aaccucauuc ugcacgacga u                                                  21

<210> SEQ ID NO 12
<211> LENGTH: 21
<212> TYPE: RNA
<213> ORGANISM: Artificial Sequence
<220> FEATURE:
<223> OTHER INFORMATION: Homo sapiens

<400> SEQUENCE: 12
aaacgucaac auugggagcc u                                              21

<210> SEQ ID NO 13
<211> LENGTH: 21
<212> TYPE: RNA
<213> ORGANISM: Artificial Sequence
<220> FEATURE:
<223> OTHER INFORMATION: Homo sapiens

<400> SEQUENCE: 13
aaguaucgag gcggacgacg a                                              21

<210> SEQ ID NO 14
<211> LENGTH: 21
<212> TYPE: RNA
<213> ORGANISM: Artificial Sequence
<220> FEATURE:
<223> OTHER INFORMATION: Homo sapiens

<400> SEQUENCE: 14
aaaaacauug aagacgucau u                                              21

<210> SEQ ID NO 15
<211> LENGTH: 21
<212> TYPE: RNA
<213> ORGANISM: Artificial Sequence
<220> FEATURE:
<223> OTHER INFORMATION: Homo sapiens

<400> SEQUENCE: 15
aaagaagauc uuggacagcg u                                              21

<210> SEQ ID NO 16
<211> LENGTH: 21
<212> TYPE: RNA
<213> ORGANISM: Artificial Sequence
<220> FEATURE:
<223> OTHER INFORMATION: Homo sapiens

<400> SEQUENCE: 16
aaaugagaag aaggaggagu c                                              21

<210> SEQ ID NO 17
<211> LENGTH: 21
<212> TYPE: RNA
<213> ORGANISM: Artificial Sequence
<220> FEATURE:
<223> OTHER INFORMATION: Homo sapiens

<400> SEQUENCE: 17
aacguggagu uuguacggaa a                                              21

<210> SEQ ID NO 18
<211> LENGTH: 21
<212> TYPE: RNA
<213> ORGANISM: Artificial Sequence
<220> FEATURE:
<223> OTHER INFORMATION: Homo sapiens

```
<400> SEQUENCE: 18
aaugaccuau gcaguucgaa a                                              21

<210> SEQ ID NO 19
<211> LENGTH: 21
<212> TYPE: RNA
<213> ORGANISM: Artificial Sequence
<220> FEATURE:
<223> OTHER INFORMATION: Homo sapiens

<400> SEQUENCE: 19
aaucucgaag ccguagucgu a                                              21

<210> SEQ ID NO 20
<211> LENGTH: 21
<212> TYPE: RNA
<213> ORGANISM: Artificial Sequence
<220> FEATURE:
<223> OTHER INFORMATION: Homo sapiens

<400> SEQUENCE: 20
aacaggauuc auggagcggg a                                              21

<210> SEQ ID NO 21
<211> LENGTH: 42
<212> TYPE: RNA
<213> ORGANISM: Artificial Sequence
<220> FEATURE:
<223> OTHER INFORMATION: Homo sapiens

<400> SEQUENCE: 21
cuguuacaau caaggucuat tuagaccuug auuguaacag tt                       42

<210> SEQ ID NO 22
<211> LENGTH: 42
<212> TYPE: RNA
<213> ORGANISM: Artificial Sequence
<220> FEATURE:
<223> OTHER INFORMATION: Homo sapiens

<400> SEQUENCE: 22
caucuacgug gguaacuuau uuaaguuacc cacguagaug uu                       42

<210> SEQ ID NO 23
<211> LENGTH: 42
<212> TYPE: RNA
<213> ORGANISM: Artificial Sequence
<220> FEATURE:
<223> OTHER INFORMATION: Homo sapiens

<400> SEQUENCE: 23
cuggauaaca cuaaguuuau uuaaacuuag uguuauccag uu                       42

<210> SEQ ID NO 24
<211> LENGTH: 42
<212> TYPE: RNA
<213> ORGANISM: Artificial Sequence
<220> FEATURE:
<223> OTHER INFORMATION: Homo sapiens

<400> SEQUENCE: 24
gcaaagaaag aagaauccgt tcggauucuu cuuucuuugc tt                       42
```

<210> SEQ ID NO 25
<211> LENGTH: 46
<212> TYPE: RNA
<213> ORGANISM: Artificial Sequence
<220> FEATURE:
<223> OTHER INFORMATION: Homo sapiens

<400> SEQUENCE: 25
gaucaaugcc cucauuaaag cttuuuaaug agggcauuga ucuutt          46

<210> SEQ ID NO 26
<211> LENGTH: 46
<212> TYPE: RNA
<213> ORGANISM: Artificial Sequence
<220> FEATURE:
<223> OTHER INFORMATION: Homo sapiens

<400> SEQUENCE: 26
gaagcaaaga aagaagaauc cttauucuuc uuucuuugcu uccatt          46

<210> SEQ ID NO 27
<211> LENGTH: 46
<212> TYPE: RNA
<213> ORGANISM: Artificial Sequence
<220> FEATURE:
<223> OTHER INFORMATION: Homo sapiens

<400> SEQUENCE: 27
ggucuuuuug acuaaaccuc uuuagguuua gucaaaaga ccaatt           46

<210> SEQ ID NO 28
<211> LENGTH: 46
<212> TYPE: RNA
<213> ORGANISM: Artificial Sequence
<220> FEATURE:
<223> OTHER INFORMATION: Homo sapiens

<400> SEQUENCE: 28
uauggccucu gucuccgagc uuuagcucgg agacagaggc cauauu          46

<210> SEQ ID NO 29
<211> LENGTH: 46
<212> TYPE: RNA
<213> ORGANISM: Artificial Sequence
<220> FEATURE:
<223> OTHER INFORMATION: Homo sapiens

<400> SEQUENCE: 29
ugucuccgag cucgccugca uuuaugcagg cgagcucgga gacauu          46

<210> SEQ ID NO 30
<211> LENGTH: 46
<212> TYPE: RNA
<213> ORGANISM: Artificial Sequence
<220> FEATURE:
<223> OTHER INFORMATION: Homo sapiens

<400> SEQUENCE: 30
aggauaagau caaugcccuu cuugaagggc auugaucuua uccuuu          46

<210> SEQ ID NO 31
<211> LENGTH: 46
<212> TYPE: RNA
<213> ORGANISM: Artificial Sequence
<220> FEATURE:
<223> OTHER INFORMATION: Homo sapiens

<400> SEQUENCE: 31
uuuggccugg cuuguuugca auuuugcaaa caagccaggc caaauu          46

<210> SEQ ID NO 32
<211> LENGTH: 46
<212> TYPE: RNA
<213> ORGANISM: Artificial Sequence
<220> FEATURE:
<223> OTHER INFORMATION: Homo sapiens

<400> SEQUENCE: 32
agaagaaagu ggaagcaaag auuucuuugc uuccacuuuc uucuuu          46

<210> SEQ ID NO 33
<211> LENGTH: 46
<212> TYPE: RNA
<213> ORGANISM: Artificial Sequence
<220> FEATURE:
<223> OTHER INFORMATION: Homo sapiens

<400> SEQUENCE: 33
uuggucuuuu ugacuaaacc uuuagguuua gucaaaaga ccaauu          46

<210> SEQ ID NO 34
<211> LENGTH: 46
<212> TYPE: RNA
<213> ORGANISM: Artifiicial Sequence
<220> FEATURE:
<223> OTHER INFORMATION: Homo sapiens

<400> SEQUENCE: 34
gcugaaugga aaaacauug auuaauguuu uuccauuca gcuctt          46

<210> SEQ ID NO 35
<211> LENGTH: 46
<212> TYPE: RNA
<213> ORGANISM: Artificial Sequence
<220> FEATURE:
<223> OTHER INFORMATION: Homo sapiens

<400> SEQUENCE: 35
gggauuuggc cuuuugauu attaucaaaa aggccaaauc ccautt          46

<210> SEQ ID NO 36
<211> LENGTH: 46
<212> TYPE: RNA
<213> ORGANISM: Artificial Sequence
<220> FEATURE:
<223> OTHER INFORMATION: Homo sapiens

<400> SEQUENCE: 36
ccuuuuugau uaaauuccug cttaggaauu uaaucaaaaa ggcctt          46

<210> SEQ ID NO 37
<211> LENGTH: 46
<212> TYPE: RNA
<213> ORGANISM: Artificial Sequence
<220> FEATURE:
<223> OTHER INFORMATION: Homo sapiens

<400> SEQUENCE: 37
cugaauggaa aaacauuga auuucaaug uuuuuccau ucaguu          46

<210> SEQ ID NO 38
<211> LENGTH: 46
<212> TYPE: RNA
<213> ORGANISM: Artificial Sequence
<220> FEATURE:
<223> OTHER INFORMATION: Homo sapiens

<400> SEQUENCE: 38
aguguaccug cuggugggc uuuagcccca ccagcaggua cacuuu          46

<210> SEQ ID NO 39
<211> LENGTH: 46
<212> TYPE: RNA
<213> ORGANISM: Artificial Sequence
<220> FEATURE:
<223> OTHER INFORMATION: Homo sapiens

<400> SEQUENCE: 39
agaggagaag aaagaugaga auuucucau cuucuucuc cucuuu          46

<210> SEQ ID NO 40
<211> LENGTH: 46
<212> TYPE: RNA
<213> ORGANISM: Artificial Sequence
<220> FEATURE:
<223> OTHER INFORMATION: Homo sapiens

<400> SEQUENCE: 40
agucugaaga gucagaugau guucaucauc ugacucuuca gacuuu          46

<210> SEQ ID NO 41
<211> LENGTH: 46
<212> TYPE: RNA
<213> ORGANISM: Artificial Sequence
<220> FEATURE:
<223> OTHER INFORMATION: Homo sapiens

<400> SEQUENCE: 41
augggauuug gccuuuuuga uuuaucaaaa aggccaaauc ccauuu          46

<210> SEQ ID NO 42
<211> LENGTH: 46
<212> TYPE: RNA
<213> ORGANISM: Artificial Sequence
<220> FEATURE:
<223> OTHER INFORMATION: Homo sapiens

<400> SEQUENCE: 42
cccagcgcca aggacaucaa guucuugaug uccuuggcgc uggguu          46

<210> SEQ ID NO 43
<211> LENGTH: 46
<212> TYPE: RNA
<213> ORGANISM: Artificial Sequence
<220> FEATURE:
<223> OTHER INFORMATION: Homo sapiens

<400> SEQUENCE: 43
guaucgaggc ggacgacgac cuuggucguc guccgccucg auacuu          46

<210> SEQ ID NO 44
<211> LENGTH: 46
<212> TYPE: RNA
<213> ORGANISM: Artificial Sequence
<220> FEATURE:
<223> OTHER INFORMATION: Homo sapiens

<400> SEQUENCE: 44
ugagcugaau ggaaaaaaca uuuauguuuu uuccauucag cucauu        46

<210> SEQ ID NO 45
<211> LENGTH: 46
<212> TYPE: RNA
<213> ORGANISM: Artificial Sequence
<220> FEATURE:
<223> OTHER INFORMATION: Homo sapiens

<400> SEQUENCE: 45
ggaaaaaaca uugaagacgu cuugacgucu ucaauguuuu uuccuu        46

<210> SEQ ID NO 46
<211> LENGTH: 46
<212> TYPE: RNA
<213> ORGANISM: Artificial Sequence
<220> FEATURE:
<223> OTHER INFORMATION: Homo sapiens

<400> SEQUENCE: 46
gaaagaugag aagaaggagg auuccuccu ucuucucauc uuucuu        46

<210> SEQ ID NO 47
<211> LENGTH: 42
<212> TYPE: RNA
<213> ORGANISM: Artificial Sequence
<220> FEATURE:
<223> OTHER INFORMATION: Homo sapiens

<400> SEQUENCE: 47
uggccuuuuu gauuaaauut taauuuaauc aaaaaggcca aa            42

<210> SEQ ID NO 48
<211> LENGTH: 42
<212> TYPE: RNA
<213> ORGANISM: Artificial Sequence
<220> FEATURE:
<223> OTHER INFORMATION: Homo sapiens

<400> SEQUENCE: 48
gcgccaagga caucaagaat tuucuugaug uccuuggcgc aa            42

<210> SEQ ID NO 49
<211> LENGTH: 42
<212> TYPE: RNA
<213> ORGANISM: Artificial Sequence
<220> FEATURE:
<223> OTHER INFORMATION: Homo sapiens

<400> SEQUENCE: 49
aaacauugaa gacgucauut taaugacguc uucaauguuu tt            42

<210> SEQ ID NO 50
<211> LENGTH: 42
<212> TYPE: RNA
<213> ORGANISM: Artificial Sequence
<220> FEATURE:
<223> OTHER INFORMATION: Homo sapiens

<400> SEQUENCE: 50
cgaccggcuc aacaagguut taaccuuguu gagccggucg tc            42

```
<210> SEQ ID NO 51
<211> LENGTH: 42
<212> TYPE: RNA
<213> ORGANISM: Artificial Sequence
<220> FEATURE:
<223> OTHER INFORMATION: Homo sapiens

<400> SEQUENCE: 51
gaagaucuug gacagcgugt tcacgcuguc caagaucuuc tt                              42

<210> SEQ ID NO 52
<211> LENGTH: 42
<212> TYPE: RNA
<213> ORGANISM: Artificial Sequence
<220> FEATURE:
<223> OTHER INFORMATION: Homo sapiens

<400> SEQUENCE: 52
caagguuauc agugugcugt tcagcacacu gauaaccuug tt                              42
```

METHODS OF REDUCING VIRUS MOLECULE LEVELS

INCORPORATION BY REFERENCE TO PRIORITY APPLICATION

This application claims priority to U.S. Provisional Application Ser. No. 62/931,962, filed Nov. 7, 2019, which is hereby incorporated herein by reference in its entirety.

REFERENCE TO SEQUENCE LISTING

The present application is being filed along with a Sequence Listing in electronic format. The Sequence Listing is provided as a file entitled ALIG032SeqListing.TXT, which was created and last modified on Apr. 15, 2021 and is 9,278 bytes in size. The information in the electronic Sequence Listing is hereby incorporated by reference in its entirety.

BACKGROUND

Field

This application relates to methods of reducing levels of virus molecules and/or treating viral infections by contacting infected cells with a therapeutic agent that targets a cellular host factor that is a target RNA or target protein involved in viral replication.

Description

Hepatitis B virus (HBV) is a DNA virus and a member of the Hepadnaviridae family. HBV infects more than 300 million worldwide and is a causative agent of liver cancer and liver disease such as chronic hepatitis, cirrhosis, and hepatocellular carcinoma. HBV infection can be acute and/or chronic. Acute HBV infection can be either asymptomatic or present with symptomatic acute hepatitis. Chronic Hepatitis B is characterized by persistent infection of liver cells by HBV that can last years and decades. HBV is classified into ten genotypes, A to J.

HBV has a partially double-stranded circular DNA of about 3.2 kilobase (kb) pairs. The HBV replication pathway has been studied in great detail (1). One part of replication includes the formation of the covalently closed circular DNA (cccDNA) form. The presence of the cccDNA gives rise to the risk of viral reemergence throughout the life of the host organism. HBV carriers can transmit the disease for many years. It is estimated that over 750,000 people worldwide die of hepatitis B each year. In addition, immunosuppressed individuals or individuals undergoing chemotherapy are especially at risk for reactivation of an HBV infection.

HBV can be transmitted by blood, semen, and/or another body fluid that contains virus. This can occur through direct blood-to-blood contact, unprotected sex, sharing of needles, and from an infected mother to her baby during the delivery process. The HBV surface antigen (HBsAg) is most frequently used to screen for the presence of this infection, as the majority of HBsAg is present in HBV virions. Currently available medications do not cure an HBV infection. Rather, the medications suppress replication of the virus.

Coronavirus disease 2019 (COVID-19) (also referred to as novel coronavirus pneumonia or 2019-nCoV acute respiratory disease) is caused by infection by SARS-CoV2, the severe acute respiratory syndrome coronavirus 2 (also referred to as novel coronavirus 2019, or 2019-nCoV). The disease was first identified in December 2019 and spread globally, causing a pandemic. Symptoms of COVID-19 include fever, cough, shortness of breath, fatigue, headache, loss of smell, nasal congestion, sore throat, sputum formation, pain in muscles or joints, chills, nausea, vomiting, and diarrhea. In severe cases, symptoms can include difficulty walking, confusion, blueish complexion, coughing up blood, decreased white blood cell count, and organ failure. Complications can include pneumonia, viral sepsis, acute respiratory distress syndrome, and kidney failure.

SARS-CoV-2 is not the only coronavirus that causes disease. It is a β-coronavirus, a genus of coronaviruses that includes other human pathogens, including the SARS-CoV (the causative agent of Severe Acute Respiratory Syndrome), MERS-CoV (the causative agent of Middle East Respiratory Syndrome), and HCoV-OC43 (one causative agent of the common cold). The infectivity of these viruses, and the severity of the diseases they cause, varies widely. β-coronavirus can also manifest as zoonotic infections, spread to and from humans and animals. Additionally, non-human species such as camels, bats, tigers, non-human primates, and rabbits can be susceptible to β-coronavirus. There is a pressing need for treatments or cures for multiple coronaviruses.

The present disclosure provides molecules useful against viruses that utilize cellular host factors for viral replication, including HBV and respiratory viruses such as coronaviruses. Accordingly, the present disclosure fulfills the need in the art for compounds that can be used to safely and effectively treat or prevent such infections in humans.

SUMMARY

Various cellular factors have now been identified as having roles in the production of certain molecules utilized by HBV and other viruses in order to replicate their genome and/or regulate the outcome of the viral infection. Oligonucleotides and siRNAs have been developed to target these cellular factors and thereby reduce production of the corresponding virus molecule(s) by the infected cell.

An embodiment provides a method of reducing a level of virus molecule produced by an infected cell, comprising:
contacting the infected cell with an effective amount of an oligonucleotide inhibitor that targets a cellular host factor to thereby inhibit production of the cellular host factor by the infected cell and reduce the amount of the virus molecule produced by the infected cell;
wherein the infected cell produces (a) at least one cellular host factor that is a target RNA or a target protein selected from a GRP78/BIP RNA, a GRP78/BIP protein, a SRSF1 RNA, a SRSF1 protein, a HNRNPA2B1 RNA, a HNRNPA2B1 protein, a RPLP1 RNA, a RPLP1 protein, a RPLP2 RNA, and a RPLP2 protein; and (b) an amount of at least one virus molecule that the virus utilizes for replication, wherein the virus molecule is a viral protein, a viral DNA or a viral RNA. In an embodiment, the virus is HBV. In another embodiment, the virus is a coronavirus. In an embodiment, the oligonucleotide inhibitor has an $EC_{50}$ value that is less than 100 nM as determined by an assay for the virus molecule.

Another embodiment provides a method of treating a viral infection, comprising:
administering a therapeutically effective amount of an oligonucleotide inhibitor to a subject in need thereof, wherein the oligonucleotide inhibitor targets a cellular host factor to thereby reduce production of the cellular host factor by infected cells of the subject;

wherein the infected cells produce at least one cellular host factor that is a target RNA or a target protein selected from a GRP78/BIP RNA, a GRP78/BIP protein, a SRSF1 RNA, a SRSF1 protein, a HNRNPA2B1 RNA, a HNRNPA2B1 protein, a RPLP1 RNA, a RPLP1 protein, a RPLP2 RNA, and a RPLP2 protein. In an embodiment, the virus causing the infection is HBV. In another embodiment, the virus causing the infection is a coronavirus. In an embodiment, the oligonucleotide inhibitor has an $EC_{50}$ value that is less than 100 nM as determined by an assay for the virus molecule.

Another embodiment provides a pharmaceutical composition for treating a viral infection in a subject, comprising:

a pharmaceutically acceptable carrier, diluent, excipient or combination thereof; and an therapeutically effective amount of an oligonucleotide inhibitor that targets at least one of a target RNA or a target protein selected from a GRP78/BIP RNA, a GRP78/BIP protein, a SRSF1 RNA, a SRSF1 protein, a HNRNPA2B1 RNA, a HNRNPA2B1 protein, a RPLP1 RNA, a RPLP1 protein, a RPLP2 RNA, and a RPLP2 protein. In an embodiment, the infecting virus is Hepatitis B virus. In another embodiment, the viral infection is COVID-19. In an embodiment, the oligonucleotide inhibitor has an $EC_{50}$ value that is less than 100 nM as determined by an assay for a virus molecule produced by the infected cell.

These and other embodiments are described in greater detail below.

BRIEF DESCRIPTION OF THE DRAWINGS

FIG. 1 illustrates that siRNAs targeting cellular RNAs can reduce the level of HBsAg made by HepG2.2.15 cells.

FIG. 1A shows schematics of host factor mRNAs, their accession numbers at the National Center of Biotechnology Information (NCBI) and the numbering of the nucleobases that is used to identify the target sequences for siRNAs in this application. The protein-coding open reading frame is denoted as a rectangle and the first adenylate of the initiation codon is the designated as nucleotide one.

FIG. 1B shows a summary of siRNA knockdowns on cell viability and HBsAg levels. Cell viability was assessed by ATP levels determined using the CellTiter-Glo reagent and the results normalized to the level in mock-treated cells. HBsAg levels were quantified using ELISA and the data normalized to the level in the mock-treated cells. The results show that siRNAs that target GRP78, SRSF1, HNRNPA2B1, and RPLP2 reduce HBsAg levels made by HepG2.2.15 cells.

FIG. 1C illustrates sample Western blot images showing that the siRNAs reduce the levels of the cellular protein that they target. The blots were probed with antisera specific to the target. L.C. denotes loading control.

FIG. 2 illustrates that siRNAs targeting cellular factors can reduce HBV S antigen levels in HepG2.2.15 cells.

FIG. 2A is a plot illustrating sample analyses of the cytotoxicities ($CC_{50}$) of siRNAs that can knock down cellular factors in HepG2.2.15 cells.

FIG. 2B is a plot illustrating sample analyses of the effective concentrations ($EC_{50}$) of two siRNAs that can knock down cellular factors in HepG2.2.15 cells, as demonstrated by siRNAs that can reduce HBsAg levels to 50% of the mock-treated samples.

FIG. 2C is a plot illustrating sample analyses of the cytotoxicities ($CC_{50}$) of siRNAs that can knock down cellular factors in HEpG2.2.15 cells.

FIG. 2D is a plot illustrating sample analyses of the effective concentrations ($EC_{50}$) of two siRNAs that can knock down cellular factors in HepG2.2.15 cells, as demonstrated by siRNAs that can reduce HBsAg levels to 50% of the mock-treated samples.

FIG. 2E is a table summarizing the cytotoxicities ($CC_{50}$) and effective concentrations ($EC_{50}$) of siRNAs that can knock down cellular factors in HepG2.2.15 cells, either singly or in combination.

FIG. 3 illustrates that siRNA targeting host factors can reduce the levels of multiple HBV molecules in HepG2.2.15 cells.

FIG. 3D is a plot illustrating that siRNAs that target HNRNPA2B1, GRP78, and SRSF1 caused a reduction of Core levels when compared to mock-treated HepG2.2.15 cells. The results illustrate quantification of the HBV proteins made by HepG2.2.15 cells after treatment with siRNAs.

FIG. 3E is a plot illustrating that siRNAs that target HNRNPA2B1, RPLP1, RPLP2, and a combination of RPLP1 and RPLP2 caused a reduction of secreted HBV DNA levels when compared to mock-treated HepG2.2.15 cells. The results illustrate quantification of the amounts of HBV DNAs found in the cell culture media. The copy number of the DNAs were determined using qPCR.

FIGS. 3A-E show that siRNA targeting host factors can reduce the levels of multiple HBV molecules in HepG2.2.15 cells. All siRNAs were introduced into cells at a final concentration of 10 nM, except for cells treated with both siRNA to RPLP1 and RPLP2, which were treated with a final concentrations of 5 nM of each set of siRNA.

FIG. 4 shows that siRNAs targeting host factors can inhibit Coronavirus virus production.

FIG. 4A shows a schematic of the experiment used to assess whether siRNAs targeting host factors can affect virion RNAs produced by HCoV-OC43 infection of HCT8 cells.

FIG. 4B shows that the host factor siRNAs tested in OC43-infected HCT 8 cells do not affect cell viability when tested at either 10 nM or 5 nM. Cell viability results were obtained using the CellTiter-Glo reagent.

FIG. 4C shows that host factor siRNAs transfected into HCT8 cells and Remdesivir added to the cultured cells can reduce HCoV-OC43 virion RNA production. The vRNAs were quantified using reverse transcription and quantitative polymerase chain reaction.

FIG. 5 illustrates the properties of several of the siRNAs targeting RPLP1 and RPLP2.

FIG. 5A shows two examples of siRNAs that inhibited the levels of HBsAg and HBeAg without affecting cell viability. The plots illustrate multiple properties: dose-dependent reduction of HBV S-antigen (HBsAg) and HBV E-antigen (HBeAg) and effects on cell viability, as determined by use of the CellTiter-Glo (CTG) reagent. The exemplified siRNAs are numbers 24 and 34, which, respectively, target RPLP1 and RPLP2 (see Table 2).

FIG. 5B. Examples of the reduction in RNAs targeted by siRNAs. The amounts of the target mRNAs were quantified by qPCR.

FIG. 5C. Examples of the reduction in proteins targeted by siRNAs. The gel images are from Western blots probed with antigen-specific antibodies. RPLP1 and RPLP2 function as heterodimers and reducing the abundance of one protein leads to a comparable reduction of the other protein. The levels of P54nrb and GAPDH serve as loading controls.

FIG. 6 illustrates that siRNAs that target host factors can reduce the amounts of Coronavirus virion RNAs.

FIG. 6A shows examples of siRNAs that target host factors can reduce HCoV-OC43 virion RNAs produced by infected cells. The siRNAs were transfected in the HCT8 cells at a final concentration of 10 nM. A positive control for the inhibition of Coronavirus infection, Remdesivir (Rem), was used at 0.9 μM. The virion RNAs (vRNAs) were quantified using a Branched DNA assay specific for OC43 RNA.

FIG. 6B shows examples of the reduction of HCoV-OV43 virion RNAs produced by cells treated with two siRNAs at a concentration of 10 nM of each siRNA. The two siRNAs are those referred to by compound number (see Table 2) in the horizontal bar, along with siRNA targeting GRP78, siGRP78. A positive control for the inhibition of Coronavirus infection, Remdesivir (Rem), was used at 0.9 μM. The vRNAs were quantified using a Branched DNA assay specific for OC43 RNA.

DETAILED DESCRIPTION

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein the term "oligonucleotide" (or "oligo") has its usual meaning as understood by those skilled in the art and thus refers to a class of compounds that includes oligodeoxynucleotides, oligodeoxyribonucleotides and oligoribonucleotides. Thus, "oligonucleotide" refers to an oligomer or polymer of ribonucleic acid (RNA) or deoxyribonucleic acid (DNA) or mimetics thereof, including reference to oligonucleotides composed of naturally-occurring nucleobases, sugars and phosphodiester (PO) internucleoside (backbone) linkages as well as "modified" or substituted oligonucleotides having non-naturally-occurring portions which function similarly, and/or including modifications such as GalNAc that increase circulation half-life and/or reduce degradation of the oligonucleotide, e.g., degradation by endonucleases, and increase cellular uptake. An "oligonucleotide inhibitor" is an oligonucleotide that at least partially inhibits production by a cell of an RNA or protein to which it is targeted.

An "antisense" oligonucleotide (ASO) is a synthetic oligonucleotide that recognizes or specifically anneals to a target RNA in a sequence-specific manner. The sequence of the target RNA recognized by the siRNA or ASO is defined by the nucleotide number of the protein-coding sequence of the mRNA, where the adenylate of the initiation codon (AUG) is designated nucleotide 1. The sequences used in this application are of a length and sequence that can recognize the target with high specificity within a cell. The specificity can be expressed by the calculated melting temperature of the duplex of 1 nM of a duplex of the siRNA and the target RNA sequence set at physiological salt (155 mM) and using the nearest neighbor parameters. The specificity can also be expressed by a thermodynamic constant for the annealed duplex, the change in Gibbs Free Energy (ΔG). A computer program to calculate Tm and thermodynamic constants for the siRNA/target duplex is available as The OligoCalc (19).

As used herein the term "siRNA" has its usual meaning as understood by those skilled in the art and thus refers to a class of oligonucleotides that are referred to as small interfering RNA, short interfering RNA and/or silencing RNA. These compounds are non-coding double-stranded RNA molecules, typically 19-25 base pairs in length, that operate within the RNA interference (RNAi) pathway and interfere with the expression of specific genes that contain complementary nucleotide sequences to the anti-sense strand of the siRNA and mediate degradation of the mRNA. The reduced level of the mRNA will decrease translation and the amount of the target protein. Reference herein to siRNA shall be understood to include reference to siRNA composed of naturally-occurring nucleobases, sugars and phosphodiester (PO) internucleoside (backbone) linkages as well as "modified" or substituted siRNA having non-naturally-occurring portions which function similarly, and/or including modifications such as GalNAc that increase circulation half-life and/or reduce degradation of the oligonucleotide, e.g., degradation by endonucleases, and increase cellular uptake.

As used herein the terms "target", "targeting" and similar terms, as used in the context of oligonucleotide inhibitor recognizing a target RNA through base pairing and have their usual meaning as understood by those skilled in the art to refer to a process by which the oligonucleotide inhibitor hybridizes to the target RNA and at least partially inhibits production of the RNA or protein to which it is targeted. For example, siRNA may cause silencing of a gene that encodes an mRNA by reducing the mRNA and thus decrease the products synthesized, including proteins, from that target RNA. Various assay techniques may be used to determine the degree to which the oligonucleotide inhibitor at least partially inhibits production of the RNA or protein to which it is targeted. Non-limiting examples of such siRNA and various RNA they target are set forth in Tables 1 and 2.

As used herein the term "virus molecule" has its usual meaning as understood by those skilled in the art and thus refers to a class of molecules made from the genome of a virus. A virus molecule is typically a viral protein, a viral DNA or a viral RNA. These molecules can be utilized or required by the virus to replicate their genome or regulate the outcome of the viral infection. For example, the term "HBV molecule" refers to a class of molecules made from the HBV genome. Examples of HBV molecules include S-antigen, E-antigen, Core-antigen, HBV RNA, and HBV DNA. In an embodiment, the virus molecule is a coronavirus molecule, such as coronavirus RNA.

As used herein the terms "cellular host factor", "cellular factor", "host factor" and similar terms have their usual meaning as understood by those skilled in the art and thus refer to an RNA or protein produced by a cell and utilized by the virus for replication. As noted above, various cellular factors have now been identified as having roles in the production of certain virus molecules utilized by HBV and other viruses in order to replicate.

Figure 3A:
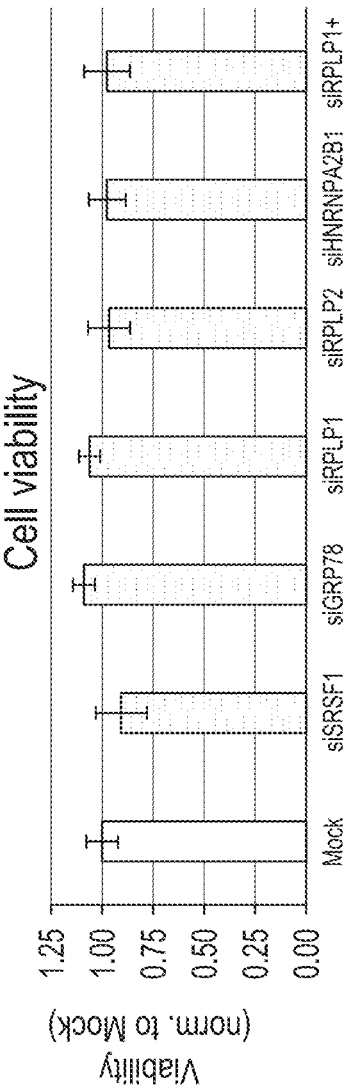
FIG. 3A is a plot illustrating that siRNAs that target HNRNPA2B1, GRP78, RPLP1, RPLP2, and SRSF1 had minimal effects on the viability of HepG2.2.15 cells. The effects on cell viability were quantified using the CellTiter-Glo reagent. All data were normalized to the amount of protein produced by mock-treated cells.

As used herein the terms "virus assay" and "viral assay" have their usual meaning as understood by those skilled in the art and thus refer to an assay that quantitatively assesses a virus molecule. For example, "HBV assay" refers to an assay that quantitatively assesses an HBV molecule or an effect of the HBV infection on the infected cell. Examples of HBV assays include HBsAg assay, HBeAg assay, HBV Core assay, HBV RNA assay, and HBV DNA assay. Likewise, a "coronavirus assay" is an example of a respiratory virus assay that quantitatively assesses a molecule or molecules of the respiratory virus or an effect of the viral infection on the infected cell. Examples of Coronavirus assays include quantitative polymerase chain reaction (qPCR) assay and a Branched DNA assay. A suitable virus assay can be used to identify a cell and/or a subject that is infected with the virus.

As used herein, a "carrier" refers to a compound or particle that facilitates the passage, delivery and/or incorporation of a compound to cells, tissues and/or bodily organs. For example, without limitation, a lipid carrier of the siRNA that can deliver the siRNA to the cytoplasm of cells. Another example is nanoparticle (LNP), a type of carrier that can encapsulate an oligonucleotide and/or siRNA to thereby protect the oligonucleotide inhibitor from degradation during passage through the bloodstream and/or to facilitate delivery to a desired organ, such as to the liver.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Methods of Reducing Virus Molecules and Treating Viral Infections

As demonstrated in the working examples below, the cellular proteins GRP78/BIP, SRSF1, HNRNPA2B1, RPLP1, and RPLP2 have now been identified as cellular host factors having roles in viral replication and infection. Various methods have now been developed for reducing the levels of virus molecules by targeting such host factors. For example, an embodiment provides a method of reducing the quantity of a virus molecule produced by an infected cell, comprising contacting the infected cell with an effective amount of an oligonucleotide inhibitor that targets at least one of a target RNA or target the reduction of the protein as described herein. Such contacting is effective to inhibit production by the infected cell of the cellular host factor and reduce the amount of the virus molecule produced by the infected cell. Those skilled in the art recognize that the methods described herein also provide descriptions of corresponding uses of the oligonucleotide inhibitors. For example, various embodiments provide an oligonucleotide inhibitor for use in a method as described herein, e.g., a method of reducing a virus level and/or treating a viral infection. Other embodiments provide an oligonucleotide inhibitor for use in preparing a medicament that is administrable to a subject by a method as described herein, e.g., a method of reducing the amount of virus produced and/or treating a viral infection.

An embodiment provides a method of reducing a level of a virus molecule produced by an infected cell, comprising:
  contacting the infected cell with an effective amount of an oligonucleotide inhibitor that targets a cellular host factor to thereby inhibit production of the cellular host factor by the infected cell and reduce the amount of the virus molecule produced by the infected cell;
  wherein the infected cell produces (a) at least one cellular host factor that is a target RNA or a target protein selected from a GRP78/BIP RNA, a GRP78/BIP protein, a SRSF1 RNA, a SRSF1 protein, a HNRNPA2B1 RNA, a HNRNPA2B1 protein, a RPLP1 RNA, a RPLP1 protein, a RPLP2 RNA, and a RPLP2 protein; and (b) an amount of at least one virus molecule that the virus utilizes for replication, wherein the virus molecule is a viral protein, a viral DNA or a viral RNA.

In an embodiment, the cell infected with the virus is a mammalian cell. For example, in an embodiment, the mammalian cell is a human cell. For an HBV infection, the infected cell is typically a cell from the liver, such as hepatocytes.

In an embodiment, the virus is HBV and the virus molecule is an HBV molecule. For example, in various embodiments the HBV molecule is an S-antigen (HBsAg), an E-antigen (HBeAg), a Core-antigen, an HBV RNA, or an HBV DNA. In an embodiment, the HBV molecule is an S-antigen (HBsAg).

In another embodiment, the virus is a respiratory virus and the virus molecule is a respiratory virus molecule. In an embodiment, the respiratory virus is a coronavirus, e.g., a coronavirus such as SARS-CoV, MERS-CoV, HCoV-OC43 (aka OC43), or SARS-CoV2 (the virus that causes Covid-19). In an embodiment, the coronavirus molecule is coronavirus RNA or the viral genome.

Various methods have also been developed for treating viral infections. For example, an embodiment provides a method of treating a viral infection, comprising:
  administering a therapeutically effective amount of an oligonucleotide inhibitor to a subject in need thereof, wherein the oligonucleotide inhibitor targets a cellular host factor to thereby reduce production of the cellular host factor by infected cells of the subject;
  wherein the infected cells produce at least one cellular host factor that is a target RNA or a target protein selected from a GRP78/BIP RNA, a GRP78/BIP protein, a SRSF1 RNA, a SRSF1 protein, a HNRNPA2B1 RNA, a HNRNPA2B1 protein, a RPLP1 RNA, a RPLP1 protein, a RPLP2 RNA, and a RPLP2 protein.

Unless the context indicates otherwise, descriptions herein of various inventive features or aspects shall be understood to apply to both such embodiments of methods of reducing levels of virus molecules produced by infected cells and methods of treating viral infections. In an embodiment, the subject infected with the virus is a mammalian subject, in which case the infected cells are mammalian cells. For example, in an embodiment, the mammalian subject is a human subject and the infected cells are human cells. In various embodiments, the methods further comprise identifying the cell and/or subject as being infected by the virus prior to contacting the infected cell with the effective amount of the oligonucleotide inhibitor and/or administering the therapeutically effective amount of oligonucleotide inhibitor to the subject.

In various embodiments, the cellular host factor produced by the infected cells of the subject is an RNA or protein as described herein. In various embodiments, the reduction in the cellular host factor by the infected cells of the subject is determined by determining a reduction in the virus molecule produced by the infected cells. In an embodiment, the oligonucleotide inhibitor reduces the level of a virus molecule produced by the infected cells and thereby reduces the viral load of the subject. In an embodiment, the virus infecting the subject is HBV and the reduction in production of the cellular host factor is indicated by a reduced level of an HBV molecule. For example, in various embodiments the HBV molecule is an S-antigen (HBsAg), an E-antigen (HBeAg), a Core-antigen, an HBV RNA, or an HBV DNA. In an embodiment, the HBV molecule is an S-antigen (HBsAg). Thus, in an embodiment, the reduction in production of the cellular host factor is indicated by a reduced level of HBsAg as determined by an HBsAg assay.

In another embodiment, the virus infecting the subject is a respiratory virus and the virus molecule is a respiratory virus molecule. In an embodiment, the respiratory virus is a coronavirus, e.g., a human coronavirus, and the respiratory virus molecule is a human coronavirus molecule. For example, in an embodiment, the coronavirus is a β-coronavirus such as SARS-CoV, SARS-CoV2, MERS-CoV, or HCoV-OC43.

In various embodiments, the oligonucleotide inhibitor targets at least one of a target RNA selected from a GRP78/BIP RNA, a SRSF1 RNA, a HNRNPA2B1 RNA, a RPLP1 RNA, and a RPLP2 RNA. In other embodiments, the oligonucleotide inhibitor targets at least one of a target protein selected from a GRP78/BIP protein, a SRSF1 protein, a HNRNPA2B1 protein, a RPLP1 protein, and a RPLP2 protein. In an embodiment, the oligonucleotide inhibitor is an anti-sense oligonucleotide (ASO) that recognizes the target RNA, wherein the target RNA includes mRNA. In another embodiment, the oligonucleotide inhibitor is a silencing RNA (siRNA) that recognizes the target RNA, wherein the target RNA includes mRNA. In various embodiments, the oligonucleotide inhibitor comprises one or more chemically-modified nucleotides that enhance binding of the oligonucleotide inhibitor to the target RNA or target protein.

Oligonucleotides and siRNAs that target at least one of a target RNA or target protein can be obtained from commercial sources, prepared by known methods or modifications thereof, and/or prepared as described elsewhere herein. Non-limiting examples of siRNAs that target GRP78/BIP, HNRNPA2B1, RPLP1, RPLP2 and SRSF1 are listed in Table 1 and Table 2 and described in the Examples below. In an embodiment, the oligonucleotide inhibitor is a siRNA as described in Table 1 and Table 2, or a modified version thereof. In various embodiments, the oligonucleotide inhibitor is modified to reduce degradation of the oligonucleotide by nucleases. In another embodiment, the oligonucleotide inhibitor is modified to enhance binding of the oligonucleotide inhibitor to the target RNA or target protein. In another embodiment, the oligonucleotide inhibitor is conjugated to amino sugars or lipids.

In an embodiment, the oligonucleotide inhibitor targets at least one of the GRP78/BIP RNA and the GRP78/BIP protein. In another embodiment, the oligonucleotide inhibitor targets at least one of the SRSF1 RNA and the SRSF1 protein. In another embodiment, the oligonucleotide inhibitor targets at least one of the HNRNPA2B1 RNA and the HNRNPA2B1 protein. In another embodiment, the oligonucleotide inhibitor targets at least one of the RPLP1 RNA and the RPLP1 protein. In another embodiment, the oligonucleotide inhibitor targets at least one of the RPLP2 RNA and the RPLP2 protein.

In an embodiment, an oligonucleotide inhibitor as described herein is administered to a subject in an amount that is effective to reduce the level of a virus molecule produced by infected cells and thereby reduce the viral load of the subject. Oligonucleotide inhibitors that target at least one of a target RNA or target protein can have an $EC_{50}$ value that is less than 100 nM, less than 50 nM, less than 30 nM, or less than 10 nM, as determined by a suitable viral assay, e.g., an HBV assay or an assay for a respiratory virus. Various suitable viral assays are known to those skilled in the art and may be selected based on the virus molecule that is selected for reduction. For example, a reduction in the level of a coronavirus RNA can be determined by measuring a reduction in virion production by the infected cell. Examples of HBV molecules include an S-antigen (HBsAg), an E-antigen (HBeAg), a Core-antigen, an HBV RNA, and an HBV DNA. In an embodiment, the HBV assay quantitatively assesses HBsAg, HBeAg, HBV Core, HBV RNA, or HBV DNA. In some situations, the selection of an HBV assay is not necessarily made on the basis of an HBV molecule that is selected for reduction, including for example situations in which the HBV molecule is not known, multiple HBV molecules are present and/or a subject is being treated for HBV. In such situations, an HBsAg assay is selected as a default HBV assay. For example, in an embodiment of a method of treating an HBV infection as described herein, the HBV assay is an HBsAg assay.

In various embodiments, levels of virus molecules can be reduced significantly by contacting a virus-infected cell with an effective amount of an oligonucleotide inhibitor as described herein. For example, the contacting of the virus-infected cell with the effective amount of the oligonucleotide inhibitor may reduce the level of the virus molecule by at least 20%, at least 30%, at least 40%, or at least 50%. In an embodiment, the cell is infected with HBV and the virus molecule is an HBV molecule. In another embodiment, the cell is infected with a coronavirus (such as a β-coronavirus) and the virus molecule is a coronavirus molecule. The reduction in the level of the virus molecule may be determined using a suitable viral assay as described elsewhere herein. Such an assay may be selected on the basis of the virus molecule for which the reduction in level is determined, again with HBsAg assay being a default HBV assay.

Some embodiments described herein relate to a method of treating a viral infection (e.g., HBV infection or respiratory virus infection such as coronavirus infection) that can include administering to a subject identified as suffering from the viral infection an effective amount of an oligonucleotide inhibitor as described herein, or a pharmaceutical composition that includes an effective amount of an oligonucleotide inhibitor as described herein. Other embodiments described herein relate to using an oligonucleotide inhibitor as described herein in the manufacture of a medicament for treating a viral infection (e.g., HBV infection or respiratory virus infection such as coronavirus infection). Still other embodiments described herein relate to the use of an oligonucleotide inhibitor as described herein or a pharmaceutical composition that includes an oligonucleotide inhibitor as described herein for treating a viral infection (e.g., an HBV infection or respiratory virus infection such as coronavirus infection).

Various embodiments provide methods of treating viral infections by administering an effective amount of an oligonucleotide inhibitor to a subject as described herein. Other embodiments provide oligonucleotide inhibitors as described herein for use in the treatment of such viral infections and/or for use in the manufacture of medicaments for such treatments of viral infections. In various embodiments, such methods and uses further comprise administering an effective amount of second therapy to the subject in combination with the oligonucleotide inhibitor. The second therapy may be selected from various therapeutic modalities for treatment of the viral infection. In an embodiment, the second therapy comprises administering an effective amount of a second therapeutic molecule to the subject in combination with the oligonucleotide inhibitor. For example, in various embodiments, the second therapeutic molecule comprises a second oligonucleotide inhibitor as described herein, a nucleoside, a nucleotide, a nucleotide prodrug, an interferon, a capsid assembly modulator, a protease inhibitor, or a combination thereof. For example, in an embodiment, the second therapeutic molecule is remdesivir. In an embodiment, the second therapeutic molecule comprises a second oligonucleotide inhibitor. In an embodiment, the second oligonucleotide inhibitor targets at least one cellular host factor. The cellular host factor targeted by the second oligonucleotide inhibitor may be the same or different from the cellular host factor targeted by the first oligonucleotide inhibitor. In an embodiment, the first oligonucleotide inhibitor targets RPLP1 and the second oligonucleotide inhibitor targets RPLP2. In another embodiment, the first oligonucleotide inhibitor targets GRP78 and the second oligonucleotide inhibitor targets RPLP1. In another embodiment, the first oligonucleotide inhibitor targets GRP78 and the second oligonucleotide inhibitor targets RPLP2.

Various routes may be used to administer an oligonucleotide inhibitor to a subject in need thereof as indicated elsewhere herein. In an embodiment, an effective amount of the oligonucleotide inhibitor, or of a pharmaceutical composition that includes the oligonucleotide inhibitor, is administered to the subject by a parenteral route. For example, in an embodiment, an effective amount of the oligonucleotide inhibitor, or of a pharmaceutical composition that includes the oligonucleotide inhibitor, is administered to the subject intravenously. In another embodiment, an effective amount of the oligonucleotide inhibitor, or of a pharmaceutical composition that includes the oligonucleotide inhibitor, is administered to the subject subcutaneously. In another embodiment, an effective amount of the oligonucleotide inhibitor, or of a pharmaceutical composition that includes the oligonucleotide inhibitor, is administered to the subject by inhalation.

Isolated Synthetic Oligonucleotide Inhibitors

Various embodiments provide an isolated synthetic oligonucleotide inhibitor having an antisense strand that hybridizes with high specificity to a target RNA as described herein. Examples of such oligonucleotide inhibitors are described in Table 2. The specificity of hybridization can be expressed by a calculated melting temperature (Tm) of at least about 48° C., about 49° C., or about 50° C. For example, in an embodiment, the specificity of hybridization is expressed by a calculated Tm of 50° C. or higher. In an embodiment, the specificity of hybridization is expressed by a calculated Tm that is greater than or equal to any of the calculated values for Tm shown in Table 2.

An embodiment provides an isolated synthetic oligonucleotide inhibitor having an antisense strand that hybridizes to a target RNA, wherein:

the target RNA is selected from a GRP78/BIP RNA, a SRSF1 RNA, a HNRNPA2B1 RNA, a RPLP1 RNA, a RPLP2 RNA; and the antisense strand is any 15-21 mer antisense strand that can hybridize with high specificity to a 15-21 length section of the target RNA selected from:
nucleobase 1379 to 1397 of the GRP78/BIP RNA,
nucleobase 51 to 69 of the SRSF1 RNA,
nucleobase 523 to 541 of the SRSF1 RNA,
nucleobase 286 to 305 of the RPLP1 RNA,
nucleobase 81 to 101 of the RPLP1 RNA,
nucleobase 283 to 303 of the RPLP1 RNA,
nucleobase 331 to 351 of the RPLP1 RNA,
nucleobase −1 to 20 of the RPLP1 RNA,
nucleobase 9 to 29 of the RPLP1 RNA,
nucleobase 74 to 94 of the RPLP1 RNA,
nucleobase 125 to 145 of the RPLP1 RNA,
nucleobase 272 to 292 of the RPLP1 RNA,
nucleobase 329 to 349 of the RPLP1 RNA,
nucleobase 135 to 155 of the RPLP2 RNA,
nucleobase 327 to 347 of the RPLP2 RNA,
nucleobase 336 to 356 of the RPLP2 RNA,
nucleobase 136 to 156 of the RPLP2 RNA,
nucleobase 190 to 210 of the RPLP2 RNA,
nucleobase 273 to 293 of the RPLP2 RNA,
nucleobase 302 to 322 of the RPLP2 RNA,
nucleobase 325 to 345 of the RPLP2 RNA,
nucleobase 52 to 72 of the RPLP2 RNA,
nucleobase 132 to 153 of the RPLP2 RNA,
nucleobase 142 to 162 of the RPLP2 RNA,
nucleobase 333 to 351 of the RPLP2 RNA,
nucleobase 56 to 74 of the RPLP2 RNA,
nucleobase 147 to 165 of the RPLP2 RNA,
nucleobase 108 to 126 of the RPLP2 RNA, and
nucleobase 120 to 138 of the RPLP2 RNA.

The nucleobases are numbered according to the positions numbered as shown for the respective target RNA as shown in FIG. 1A. In various embodiment, the specificity of hybridization is expressed by a calculated Tm of at least about 48° C., about 49° C., or about 50° C. For example, in an embodiment, the specificity of hybridization is expressed by a calculated Tm of 50° C. or higher, such as a calculated Tm that is greater than or equal to any one of the calculated values for Tm shown in Table 2.

In various embodiments the antisense strand of the isolated synthetic oligonucleotide inhibitor is any 15-21 mer, 16-21 mer, 17-21 mer, 18-21 mer, 19-21 mer or 20-21 mer antisense strand within the antisense strand of any one of SEQ ID NOS. 21-52, with the proviso that the antisense strand of the isolated synthetic oligonucleotide is not any one of SEQ ID NOS. 1-20. For example, in an embodiment, the antisense strand of the isolated synthetic oligonucleotide inhibitor is any 15-21 mer antisense strand within the antisense strand of any one of SEQ ID NOS. 21-42, 44-45, 47-50 and 52. In another embodiment, the antisense strand of the isolated synthetic oligonucleotide inhibitor is any 17-21 mer antisense strand within the antisense strand of any one of SEQ ID NOS. 21-42, 44-50 and 52.

Discussion of Methods of Reducing Virus Molecules and Treating Viral Infections

Viruses are intracellular parasites that depend on the host cells for many metabolites and factors needed for their reproduction and propagation. The cellular host factors are potential targets for therapeutic intervention, as long as they are not essential for the health of the cell. Targeting cellular proteins to reduce viral infection may be less likely to select for resistant viruses when compared to direct-acting antivirals, as the production of the cellular molecules is not typically subject to error-prone synthesis that typifies viral nucleic acid synthesis (2).

HBV is among the smallest of the enveloped viruses (1). HBV attacks liver cells and its infection can be either acute and cleared by the host, or chronic. Chronic infections and the resulting inflammatory responses can lead to patients developing hepatitis, liver cirrhosis and hepatocellular carcinoma. Over 180 million people worldwide are chronically infected by HBV. While existing drugs that can inhibit the HBV polymerase are available and are effective in reducing viral load, they do not result in cures of the viral infection.

HBV gain entry to liver cells through the liver-specific bile acid transporter named the sodium taurocholate co-transporting polypeptide (NCTP) (3). The nucleocapsid released into the cells contains a relaxed partial double-stranded DNA genome covalently attached to the viral polymerase that can convert the partial double-stranded DNA to a covalently-closed circle, called the cccDNA. The cccDNA is the template for transcription of a nest of HBV RNAs that can be processed and then translated to form several proteins, or the HBV pre-genomic RNA that can be replicated to form the HBV DNA (1). The first HBV protein to be discovered is the HBV surface antigen (HBsAg), which is secreted to affect the immune response as well as assembled around the nucleocapsid to form the infectious virus. The Core protein (also known as the Core antigen) is the structural protein that assembles around the HBV genome to form the icosahedral nucleocapsid. The E-antigen (HBeAg) is produced from an RNA splice variant that contains a leader peptide fused to Core to enable the secretion of the E-antigen from the infected cell, with a possible consequence of interfering with the host immune response. HBV also produces its own DNA polymerase, a reverse transcriptase that can synthesize DNA from either RNA or DNA templates. The HBV protein referred to as HBX is a multi-functional protein that can regulate cellular signaling as well as contribute to liver pathology.

HBV replication has been extensively studied in cultured cells. The human hepatoblastoma cell line, HepG2 cells, can be infected with HBV virions, especially when they over-express the NCTP receptor (4). HepG.2.2.15 cells derived from HepG2 cells containing integrated copies of the HBV genome have also been used to produce HBV molecules and form infectious virions (5).

It is believed that cellular proteins play important roles throughout the HBV replication/infection process. Several of these host factors have been identified, including ones that play roles in the synthesis, folding, modification, and trafficking of the HBV proteins (6). Host factors that interact with the processing of HBV nucleic acids have also been identified, although their roles in HBV infection are less well-studied and understood. Host proteins are known to interact with the epsilon element, an RNA motif present at the two termini of the HBV pre-genomic RNA and at the 3' terminus of the HBV mRNAs (7). The Epsilon element is required for HBV nucleic acid synthesis and encapsidation (8).

The RNAs and proteins known as GRP78/BIP RNA, GRP78/BIP protein, SRSF1 RNA, SRSF1 protein, HNRNPA2B1 RNA, HNRNPA2B1 protein, RPLP1 RNA, RPLP1 protein, RPLP2 RNA, and RPLP2 protein are known but oligonucleotide inhibitors have not been previously identified as candidates for targeting to reduce HBV or respiratory virus molecule levels and/or for treating HBV infection or respiratory virus infection. The GRP78/BIP protein, which may be referred to as GRP78 or as BIP, is believed to be a protein chaperone that regulates the recognition of mis-folded proteins that can affect cell survival, protein synthesis, and protein degradation (9). GRP78 protein levels may be elevated during HBV infection, and may associate with over-expressed HBsAg (10). SRSF1 protein is an RNA-binding protein that impacts RNA splicing, RNA transport and translatability, and can regulate nonsense-mediated mRNA decay (11). HNRNPA2B1 protein recognizes RNA, including those with N6-methylated adenylates to regulate RNA stability, processing, and translatability (12). HBV RNAs have been shown to possess N6-methyl-adenylates at the base of the epsilon element implicated in HBV RNA stability, replication and translatability (13). HNRNPA2B1 may also be implicated in the regulation of proinflammatory cytokine production that can activate host innate immune response to viral infection (14). RPLP2 protein is a ribosome-associated protein that is thought to regulate the efficiency of translational elongation (15). RPLP2 protein functions in complex with two additional proteins, RPLP0 and RPLP1 to comprise a structure named the acidic ribosome stalk that can interact with translation elongation factors to enhance the translation of some trans-membrane proteins (16). Both RPLP1 and RPLP2 are implicated in the production of wild-type levels of the envelope proteins from several positive-strand RNA viruses, and both affect infectivity (17, 18).

Pharmaceutical Compositions

Some embodiments described herein relate to a pharmaceutical composition that can include an oligonucleotide inhibitor as described herein, and a pharmaceutically acceptable carrier, diluent, excipient or combination thereof. For example, an embodiment provides a pharmaceutical composition for treating a viral infection (e.g., an HBV infection or respiratory virus infection such as coronavirus infection), comprising:

a pharmaceutically acceptable carrier, diluent, excipient or combination thereof; and an effective amount of one or more of an oligonucleotide inhibitor that targets at least one of a target RNA or a target protein selected from a GRP78/BIP RNA, a GRP78/BIP protein, a SRSF1 RNA, a SRSF1 protein, a HNRNPA2B1 RNA, a HNRNPA2B1 protein, a RPLP1 RNA, a RPLP1 protein, a RPLP2 RNA, and a RPLP2 protein.

In an embodiment, the oligonucleotide inhibitor has an $EC_{50}$ value that is less than 100 nM as determined by a suitable assay (e.g., an HBV assay or an assay for a respiratory virus such as a coronavirus assay).

Those skilled in the art will understand that the oligonucleotide inhibitor that are included in the pharmaceutical composition can be any one or more of the various oligonucleotide inhibitors that target at least one of a target RNA or a target protein as described elsewhere herein. For example, in an embodiment, the siRNA in the pharmaceutical composition is an siRNA as described in Table 1 or a modified version thereof. In another embodiment, the siRNA in the pharmaceutical composition is an siRNA as described in Table 2 or a modified version thereof.

Proper formulation of the pharmaceutical composition is dependent upon the route of administration chosen. Techniques for formulation and administration of the oligonucleotide inhibitors described herein are known to those skilled in the art. Multiple techniques of administering oligonucleotide inhibitors exist in the art including but not limited to parenteral delivery, such as by inhalation, intravenous or subcutaneous delivery. Pharmaceutical compositions will generally be tailored to the specific intended route of administration. For example, in an embodiment, the pharmaceutical composition is in a form suitable for administration to a subject via parenteral delivery. In various embodiments such a parenteral delivery form includes a carrier that enhances delivery. For example, in an embodiment the oligonucleotide inhibitor is encapsulated in lipids that protect the oligonucleotide inhibitor from degradation during passage through the bloodstream and/or facilitates delivery to a desired organ, such as to the liver.

EXAMPLES

Additional embodiments are disclosed in further detail in the following examples, which are not in any way intended to limit the scope of the claims.

Examples 1-20

A series of siRNA that target cellular host factors to reduce HBV molecule levels were prepared or obtained from commercial sources. Table 1 describes the sequence for each siRNA and the corresponding target RNA.

TABLE 1

| siRNA SEQ ID NO | siRNA sense-strand (5-3') | Target RNA | Target nucl. no[1] | Tm (° C.)[2] | ΔG (Kcal/mol)[3] |
|---|---|---|---|---|---|
| 1 | AAGCGCAUUGAUACUAGAAAU | GRP78/BIP | 1671 to 1689 | 56.5 | 21.4 |
| 2 | AGGAACCAUCCCGUGGCAUAA | GRP78/BIP | 1147 to 1165 | 66.3 | 24.7 |
| 3 | AAGAAAGAAGGUUACCCAUGC | GRP78/BIP | 485 to 503 | 62.6 | 22.6 |
| 4 | AAAGAUGAAGCUGUAGCGUAU | GRP78/BIP | 1170 to 1188 | 61.8 | 22.6 |
| 5 | AACGGUGGAAAUUUCGGACCA | HNRNPA2B1 | 617 to 633 | 64.8 | 25.6 |
| 6 | AAGCUGUUUGUUGGCGGAAUU | HNRNPA2B1 | 301 to 321 | 62.5 | 24.6 |
| 7 | AAGGAGAGUAGUUGAGCCAAA | HNRNPA2B1 | 227 to 245 | 64.4 | 22.9 |
| 8 | AAGAGGAGGAUCUGAUGGAUA | HNRNPA2B1 | 646 to 665 | 63.8 | 21.8 |
| 9 | AAUGACAUGGGCUUUGGUCUU | RPLP1 | 317 to 335 | 65.2 | 23.9 |
| 10 | AAAAGAAGAAUCCGAGGAGUC | RPLP1 | 292 to 311 | 62.4 | 23.0 |
| 11 | AACCUCAUUCUGCACGACGAU | RPLP1 | 39 to 57 | 64.3 | 25.1 |
| 12 | AAACGUCAACAUUGGGAGCCU | RPLP1 | 157 to 176 | 67.3 | 25.3 |
| 13 | AAGUAUCGAGGCGGACGACGA | RPLP2 | 92 to 110 | 69.4 | 28.0 |
| 14 | AAAAACAUUGAAGACGUCAUU | RPLP2 | 245 to 165 | 53.5 | 21.2 |
| 15 | AAAGAAGAUCUUGGACAGCGU | RPLP2 | 70 to 89 | 64.0 | 23.9 |
| 16 | AAAUGAGAAGAAGGAGGAGUC | RPLP2 | 287 to 305 | 63.4 | 22.2 |
| 17 | AACGUGGAGUUUGUACGGAAA | SRSF1 | 477 to 495 | 62.2 | 24.4 |
| 18 | AAUGACCUAUGCAGUUCGAAA | SRSF1 | 502 to 522 | 61.4 | 23.2 |
| 19 | AAUCUCGAAGCCGUAGUCGUA | SRSF1 | 618 to 637 | 66.6 | 25.8 |
| 20 | AACAGGAUUCAUGGAGCGGGA | SRSF1 | 2246 to 2264 | 68.5 | 25.6 |

[1] The first adenylate in the initiation codon (AUG) of the target mRNA is designated as nt. 1.
[2] Tm was determined for 1 nM double-stranded RNA in 155 mM salt (Na+) and using Nearest Neighbor parameters.
[3] ΔG was calculated for 1 nM of annealed dsRNA at thermodynamic constant conditions: 1M NaCl at 25° C., pH 7.0.

Examples 21-52

A series of siRNA that target cellular factors to reduce virus molecule levels were prepared. Table 2 describes the sequence for each siRNA and the corresponding target RNA.

TABLE 2

| siRNA SEQ ID NO | Strand | siRNA Sequence (5' to 3') | Target RNA | Target nucl. no[1] | Tm (° C.)[2] | ΔG (Kcal/mol)[3] |
|---|---|---|---|---|---|---|
| 21 | sense | CUGUUACAAUCAAGGUCUAUU | GRP78 | 1379 to 1397 | 58.0 | 20.5 |
|  | antisense | UAGACCUUGAUUGUAACAGTT |  |  |  |  |
| 22 | sense | CAUCUACGUGGGUAACUUAUU | SRSF1 | 51 to 69 | 61.1 | 21.9 |
|  | antisense | UAAGUUACCCACGUAGAUGUU |  |  |  |  |

TABLE 2-continued

| siRNA SEQ ID NO | Strand | siRNA Sequence (5' to 3') | Target RNA | Target nucl. no[1] | Tm (° C.)[2] | ΔG (Kcal/mol)[3] |
|---|---|---|---|---|---|---|
| 23 | sense antisense | CUGGAUAACACUAAGUUUAUU UAAACUUAGUGUUAUCCAGUU | SRSF1 | 523 to 541 | 54.8 | 19.4 |
| 24 | sense antisense | GCAAAGAAAGAAGAAUCCGTT CGGAUUCUUCUUUCUUUGCTT | RPLP1 | 286 to 305 | 57.1 | 22.5 |
| 25 | sense antisense | GAUCAAUGCCCUCAUUAAAGCTT UUUAAUGAGGGCAUUGAUCUUTT | RPLP1 | 81 to 101 | 62.8 | 24.8 |
| 26 | sense antisense | GAAGCAAAGAAAGAAGAAUCCTT AUUCUUCUUUCUUUGCUUCCATT | RPLP1 | 283 to 303 | 59.3 | 23.9 |
| 27 | sense antisense | GGUCUUUUUGACUAAACCUCUTT AGGUUUAGUCAAAAGACCAATT | RPLP1 | 331 to 351 | 61.7 | 24.0 |
| 28 | sense antisense | UAUGGCCUCUGUCUCCGAGCUUU AGCUCGGAGACAGAGGCCAUAUU | RPLP1 | −1 to 20 | 73.3 | 28.9 |
| 29 | sense antisense | UGUCUCCGAGCUCGCCUGCAUUU AUGCAGGCGAGCUCGGAGACAUU | RPLP1 | 9 to 29 | 74.5 | 31.1 |
| 30 | sense antisense | AGGAUAAGAUCAAUGCCCUUCUU GAAGGGCAUUGAUCUUAUCCUUU | RPLP1 | 74 to 94 | 64.3 | 24.7 |
| 31 | sense antisense | UUUGGCCUGGCUUGUUUGCAAUU UUGCAAACAAGCCAGGCCAAAUU | RPLP1 | 125 to 145 | 68.8 | 28.4 |
| 32 | sense antisense | AGAAGAAAGUGGAAGCAAAGAUU UCUUUGCUUCCACUUUCUUCUUU | RPLP1 | 272 to 292 | 62.5 | 25.0 |
| 33 | sense antisense | UUGGUCUUUUUGACUAAACCUUU AGGUUUAGUCAAAAAGACCAAUU | RPLP1 | 329 to 349 | 60.1 | 23.9 |
| 34 | sense antisense | GCUGAAUGGAAAAAACAUUGAUU AAUGUUUUUUCCAUUCAGCUCTT | RPLP2 | 135 to 155 | 57.5 | 23.9 |
| 35 | sense antisense | GGGAUUUGGCCUUUUUGAUUAUU AUCAAAAAGGCCAAAUCCCAUTT | RPLP2 | 327 to 347 | 61.4 | 24.7 |
| 36 | sense antisense | CCUUUUUGAUUAAAUUCCUGCTT AGGAAUUUAAUCAAAAAGGCCTT | RPLP2 | 336 to 356 | 56.3 | 23.2 |
| 37 | sense antisense | CUGAAUGGAAAAAACAUUGAAUU UUCAAUGUUUUUUCCAUUCAGUU | RPLP2 | 136 to 156 | 54.0 | 22.8 |
| 38 | sense antisense | AGUGUACCUGCUGGUGGGGCUUU AGCCCCACCAGCAGGUACACUUU | RPLP2 | 190 to 210 | 77.5 | 29.8 |
| 39 | sense antisense | AGAGGAGAAGAAAGAUGAGAAUU UUCUCAUCUUUCUUCUCCUCUUU | RPLP2 | 273 to 293 | 62.3 | 24.0 |
| 40 | sense antisense | AGUCUGAAGAGUCAGAUGAUGUU CAUCAUCUGACUCUUCAGACUUU | RPLP2 | 302 to 322 | 63.7 | 24.3 |
| 41 | sense antisense | AUGGGAUUUGGCCUUUUUGAUUU AUCAAAAAGGCCAAAUCCCAUUU | RPLP2 | 325 to 345 | 62.2 | 25.2 |
| 42 | sense antisense | CCCAGCGCCAAGGACAUCAAGUU CUUGAUGUCCUUGGCGCUGGGUU | RPLP2 | 52 to 72 | 73.0 | 29.9 |
| 43 | sense antisense | GUAUCGAGGCGGACGACGACCUU GGUCGUCGUCCGCCUCGAUACUU | RPLP2 | 92 to 112 | 73.6 | 31.6 |
| 44 | sense antisense | UGAGCUGAAUGGAAAAAACAUUU AUGUUUUUUCCAUUCAGCUCAUU | RPLP2 | 132 to 153 | 59.1 | 24.2 |
| 45 | sense antisense | GGAAAAAACAUUGAAGACGUCUU GACGUCUUCAAUGUUUUUUCCUU | RPLP2 | 142 to 162 | 58.4 | 24.6 |
| 46 | sense antisense | GAAAGAUGAGAAGAAGGAGGAUU UCCUCCUUCUUCUCAUCUUUCUU | RPLP2 | 282 to 302 | 63.9 | 24.6 |
| 47 | sense antisense | UGGCCUUUUUGAUUAAAUUUU AAUUUAAUCAAAAAGGCCAAA | RPLP2 | 333 to 351 | 51.1 | 20.2 |

TABLE 2-continued

| siRNA SEQ ID NO | Strand | siRNA Sequence (5' to 3') | Target RNA | Target nucl. no[1] | Tm (° C.)[2] | ΔG (Kcal/mol)[3] |
|---|---|---|---|---|---|---|
| 48 | sense<br>antisense | GCGCCAAGGACAUCAAGAATT<br>UUCUUGAUGUCCUUGGCGCAA | RPLP2 | 56 to 74 | 65.7 | 25.2 |
| 49 | sense<br>antisense | AAACAUUGAAGACGUCAUUTT<br>AAUGACGUCUUCAAUGUUUTT | RPLP2 | 147 to 165 | 53.5 | 21.2 |
| 50 | sense<br>antisense | CGACCGGCUCAACAAGGUUTT<br>AACCUUGUUGAGCCGGUCGTC | RPLP2 | 108 to 126 | 68.1 | 26.7 |
| 51 | sense<br>antisense | GAAGAUCUUGGACAGCGUGTT<br>CACGCUGUCCAAGAUCUUCTT | RPLP2 | 72 to 90 | 64.0 | 24.1 |
| 52 | sense<br>antisense | CAAGGUUAUCAGUGUGCUGTT<br>CAGCACACUGAUAACCUUGTT | RPLP2 | 120 to 138 | 62.4 | 22.6 |

[1]The first adenylate in the initiation codon (AUG) of the target mRNA is designated as nt. 1.
[2]Tm was determined for 1 nM double-stranded RNA in 155 mM salt (Na+) and using Nearest Neighbor parameters.
[3]ΔG was calculated for 1 nM of annealed dsRNA at thermodynamic constant conditions: 1M NaCl at 25° C., pH 7.0.

Example A1

The cellular proteins GRP78/BIP, SRSF1, HNRNPA2B1, RPLP1, and RPLP2 were identified as having roles in HBV replication and infection. Various siRNAs and combinations thereof targeting the RNAs encoding these proteins were contacted with HepG2.2.15 cells at a final concentration of 7.5 nM. The introduction of the siRNAs had minimal effects on cell viability (see FIG. 1B). As shown in FIGS. 1B and 1C, these siRNAs reduced the level of HBV molecules, as indicated by a reduction in S-antigen (HBsAg) by more than 50% as compared to mock, as determined by an HBsAg assay. Knockdown of RPLP1 reduced HBsAg levels more than did knockdown of RPLP2. Furthermore, siRNA knocking down both RPLP1 and RPLP2 in HepG2.2.15 cells resulted in an additional decrease in HBsAg levels when compared to cells treated with siRNA targeted to RPLP1 or RPLP2 alone, indicating that the cellular factors may act in concert for optimal HBsAg accumulation. Likewise, siRNA targeting both GRP78 and RPLP2 reduced the level of HBsAg more than did the knockdown of either individual factor.

Example A2

The EC$_{50}$ values of several siRNAs and combinations of siRNAs targeting HNRNPA2B1, GRP78, RPLP1, RPLP2, and/or SRSF1 were determined with respect to the ability to reduce HBsAg levels in HepG2.2.15 cells. See FIGS. 2A-E. The siRNAs targeting GRP78 were found to reduce HBsAg level with an EC$_{50}$ value of 1 nM with no effects on the viability of the HepG2.2.15 cells (FIGS. 2A, 2B, and 2E). The effect on HBsAg levels of the siRNA targeting RPLP1 was likewise highly potent, producing an EC$_{50}$ value of about 0.9 nM, with CC$_{50}$ being in excess of 100 nM (FIGS. 2C, 2D, and 2E). SiRNAs that target both RPLP1 and RPLP2 had EC$_{50}$ values of about 0.3 nM and CC$_{50}$ values in excess of 100 nM. siRNAs targeting SRSF1 and RPLP2 also had EC$_{50}$ values of about 1.5 nM or less, with CC$_{50}$ values in excess of 100 nM (FIGS. 2D and 2E).

Example A3

Figure 3B:
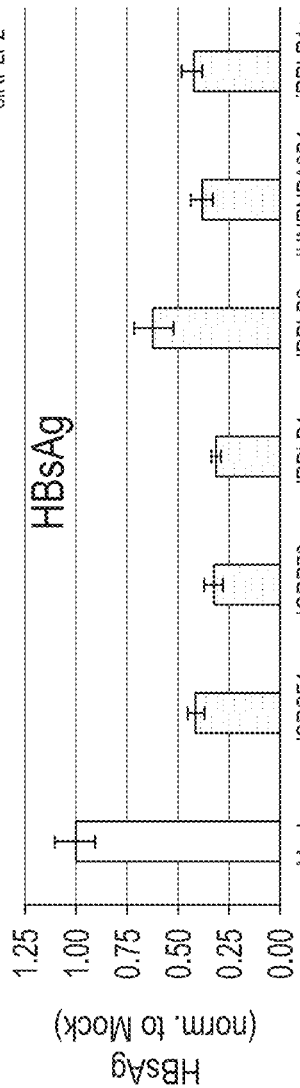
FIG. 3B is a plot illustrating that siRNAs that target HNRNPA2B1, GRP78, RPLP1, RPLP2, and SRSF1 caused a reduction of HBsAg levels when compared to mock-treated HepG2.2.15 cells. The HBV proteins produced by HepG2.2.15 cells after treatment with siRNAs were quantified using ELISAs.
Figure 3C:
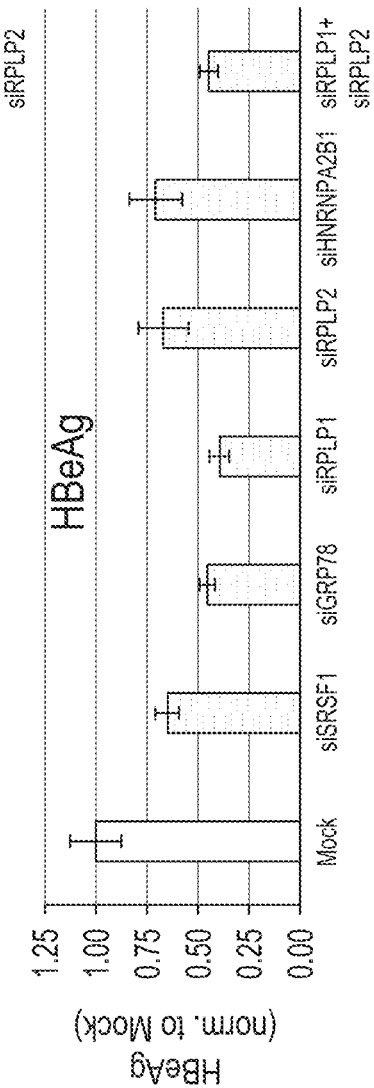
FIG. 3C is a plot illustrating that siRNAs that target HNRNPA2B1, GRP78, RPLP1, RPLP2, and SRSF1 caused a reduction of HBeAg levels when compared to mock-treated HepG2.2.15 cells. The results illustrate quantification of the HBV proteins made by HepG2.2.15 cells after treatment with siRNAs. HBeAg in the cell culture media was assessed using ELISAs.

The ability of siRNAs targeting host factors that then results in the reduced production of multiple HBV molecules was evaluated by quantifying the amount of HBsAg, HBeAg, and Core protein produced by HepG2.2.15 cells after contacting with 10 nM of siRNAs that target HNRNPA2B1, GRP78, RPLP1, RPLP2, and SRSF1. We also contacted the cells with 5 nM of each set of siRNAs that targets both RPLP1 and RPLP2. The level of HBsAg, HBeAg, and Core were all determined using ELISAs. The introduction of the siRNAs had minimal effects on cell viability or cytotoxicity (FIG. 3A). The siRNAs caused a reduction of HBsAg levels when compared to mock-treated cells, with knockdowns of GRP78 and RPLP1 causing the largest reduction, and knockdown of HNRNPA2B1 having an intermediate effect (FIG. 3B). Knockdowns of GRP78 and RPLP1 again caused the largest decrease on the level of HBeAg (FIG. 3C), with the decrease in HBeAg associated with the knockdown of HNRNPA2B1 being more modest (FIG. 3C). For the Core antigen, the knockdown of SRSF1 caused the most pronounced decrease. The siRNAs that knocked down both RPLP1 and RPLP2 produced the largest reductions in HBsAg and HBeAg but did not discernably affect the level of Core protein (FIG. 3C-3D). Finally, knockdowns of RPLP1 and RPLP2 caused a reduction in the amount of secreted HBV DNAs (FIG. 3E).

Altogether, these results show that the cellular factors can contribute to the levels of multiple HBV molecules in a hepatocyte model for HBV infection and that specific host factor(s) can contribute to the accumulation of an HBV molecule. Importantly, siRNAs and oligonucleotides that target the RNA encoding the host factor can decrease the levels of HBV molecules that are needed for successful infection.

Example A4

The host factors we identified to affect HBV replication also have roles in coronavirus infection. The human coronavirus OC43 is a member of the β-coronavirus genus, the same as the highly pathogenic SARS-CoV and SARS-CoV2 (20). We established procedures for OC43 to infect HCT8, a human colon epithelial cell line, as coronaviruses can infect human intestinal tract and cause diarrhea. HCT8 cells express GRP78, RPLP1/2, SRSF1, and HNRNPA2B1 and transfection of siRNAs targeting these host factors resulted in the specific knockdown of these host factors. To examine the effects of siRNAs on OC43 infection, HCT8 cells were first infected virus and then transfected with siRNAs and the amount of virus produced from the infection was quantified using reverse transcription-quantitative polymerase chain reaction (RT-qPCR) that had primers specific to the OC43 N gene (FIG. 4A). A positive control for the experiment was to assess the effects of Remdesivir, a nucleotide prodrug that can inhibit coronavirus replication (21). Finally, cell viability was also assessed using the CellTiter-Glo reagent. In these experiments, Remdesivir at 0.5 M was able to reduce OC43 virion production to less than 5%. In addition, siRNAs targeting RPLP1 and GRP78 reduced OC43 RNAs without obvious detrimental effects on the viability of HCT8 cells (FIGS. 4B and 4C). In other experiments, knockdown of RPLP2 and SRSF1 also reduced OC43 RNA relative to the mock-treated cells. These results demonstrate that RPLP1/2, GRP78, and SRSF1 have roles for Coronavirus infection and that siRNAs targeting the host factors needed for HBV infection can also inhibit Coronavirus infection.

Example A5

A library of siRNAs that target GRP78, SRSF1, RPLP1 and RPLP2 was designed and synthesized. This library was biased to favor RPLP1 and RPLP2 because these proteins are nonessential in somatic cells and they function upstream of GRP78. That is, viral protein synthesis that failed due to a deficiency in the RPLP1 and RPLP2 proteins cannot be rescued by the chaperon protein GRP78.

Example A6

The library of siRNAs of Example A5 were tested for the reduction of HBsAg secreted by HepG2.2.15 cells and in HBV virions. As summarized in Table 3, 1 of the siRNAs targeted GRP78, 2 targeted SRSF2, 10 targeted RPLP1, and 19 targeted RPLP2, and all were found to reduce HBsAg levels with $EC_{50}$ values of less than 10 nM. In fact, the majority of the siRNAs had $EC_{50}$ values of less than 1 nM. Furthermore, none of the siRNAs had apparent cytotoxicity at the highest concentration tested, 80 nM (Table 3). Finally, the effective siRNAs reduced the levels of another key HBV molecule, HBeAg. Examples of the dose responses for HBsAg and HBeAg reduction and the cytotoxicity profile for two siRNAs (SEQ ID NOS 24 and 34) are shown in FIG. 5A.

TABLE 3

| SEQ ID NO | Target | $EC_{50}$, Extracell. HBsAg reduction (pM) | $CC_{50}$, HepG2.2.15 cell viability (nM) | HBeAg reduction HepG2.2.15 cells* (%) | Target RNA reduction in HepG2.2.15 cells* (%) | Target protein reduction in HepG2.2.15 cells* (%) | OC43 vRNA reduction* (%) | OC43 vRNA reduction siRNA and siGRP78* (%) |
|---|---|---|---|---|---|---|---|---|
| 21 | GRP78 | 1600 | >80 | 61.5 ± 10 | 90 ± 3 | 59 ± 2 | 89 ± 8 | 90 ± 4 |
| 22 | SRSF1 | 900 | >80 | 33.5 ± 5 | 71 ± 1 | 92 ± 20 | 36 ± 3 | 85 ± 4 |
| 23 | SRSF1 | 3900 | >80 | 29.8 ± 3 | ND | 81 ± 11 | ND | ND |
| 24 | RPLP1 | 359 | >80 | 66 ± 2 | 80 ± 1 | 48 ± 3 | 89 ± 8 | 94 ± 4 |
| 25 | RPLP1 | 1830 | >80 | 60 ± 3 | 74 ± 6 | 53 ± 12 | 80 ± 7 | 88 ± 3 |
| 26 | RPLP1 | 376 | >80 | 64 ± 3 | 86 ± 1 | 72 ± 17 | 91 ± 3 | 95 ± 1 |
| 27 | RPLP1 | 110 | >80 | 55 ± 5 | 72 ± 7 | 51 ± 9 | 94 ± 4 | 95 ± 2 |
| 28 | RPLP1 | 190 | >80 | 30 ± 4 | 80 ± 2 | 58 ± 7 | 48 ± 12 | 71 ± 6 |
| 29 | RPLP1 | 386 | >80 | 58 ± 3 | 75 ± 1 | 52 ± 4 | 87 ± 10 | 92 ± 3 |
| 30 | RPLP1 | 690 | >80 | 58 ± 4 | 78 ± 3 | 45 ± 8 | 90 ± 6 | 84 ± 6 |
| 31 | RPLP1 | 12 | >80 | ND | 84 ± 4 | 37 ± 7 | 82 ± 4 | 82 ± 6 |
| 32 | RPLP1 | 525 | >80 | 32 ± 6 | 80 ± 7 | 71 ± 8 | 87 ± 4 | 86 ± 4 |
| 33 | RPLP1 | 1537 | >80 | ND | 83 ± 6 | 28 ± 4 | ND | ND |
| 34 | RPLP2 | 150 | >80 | 74 ± 4 | 93 ± 1 | 62.5 ± 3 | 86 ± 3 | 86 ± 5 |
| 35 | RPLP2 | 10 | >80 | 69 ± 3 | 98 ± 0 | 78 ± 16 | 94 ± 6 | 96 ± 1 |
| 36 | RPLP2 | 9200 | >80 | 26 ± 5 | 94 ± 1 | 57 ± 3 | ND | 87 ± 6 |
| 37 | RPLP2 | 49 | >80 | 53 ± 3 | 98 ± 1 | 71 ± 10 | 94 ± 2 | 88 ± 5 |
| 38 | RPLP2 | 76 | >80 | ND | 96 ± 1 | 55 ± 2 | 39 ± 6 | 61 ± 14 |
| 39 | RPLP2 | 103 | >80 | 59 ± 4 | 96 ± 1 | 48 ± 9 | 91 ± 2 | 86 ± 6 |
| 40 | RPLP2 | 114 | >80 | 56 ± 3 | 98 ± 1 | 54 ± 2 | 89 ± 5 | 79 ± 15 |
| 41 | RPLP2 | 208 | >80 | 40 ± 4 | 97 ± 1 | 58 ± 2 | 89 ± 5 | 81 ± 7 |
| 42 | RPLP2 | 385 | >80 | 42 ± 2 | 95 ± 1 | 50 ± 4 | 57 ± 5 | 85 ± 7 |
| 43 | RPLP2 | 182 | >80 | 70 ± 5 | 94 ± 2 | 45 ± 4 | 94 ± 1 | 92 ± 2 |
| 44 | RPLP2 | 84 | >80 | 30 ± 4 | 99 ± 1 | 59 ± 11 | ND | 92 ± 2 |
| 45 | RPLP2 | 13 | >80 | 42 ± 5 | 98 ± 1 | 61 ± 7 | ND | 89 ± 2 |
| 46 | RPLP2 | 1100 | >80 | 44 ± 5 | 98 ± 1 | 56 ± 8 | ND | 87 ± 4 |
| 47 | RPLP2 | 70 | >80 | 38 ± 5 | 97 ± 3 | 67 ± 5 | ND | 89 ± 2 |
| 48 | RPLP2 | 100 | >80 | 32 ± 5 | 97 ± 0 | 54 ± 8 | ND | 88 ± 5 |
| 49 | RPLP2 | 26 | >80 | 32 ± 6 | 98 ± 1 | 59 ± 4 | ND | 91 ± 3 |
| 50 | RPLP2 | 95 | >80 | 42 ± 5 | 98 ± 1 | 48 ± 2 | ND | 91 ± 2 |
| 51 | RPLP2 | 100 | >80 | 32 ± 4 | 98 ± 0 | 56 ± 5 | ND | 90 ± 2 |
| 52 | RPLP2 | 60 | >80 | 54 ± 5 | 98 ± 1 | 58 ± 1 | ND | 91 ± 2 |

*10 nM siRNA was transfected into cells
ND: Not determined

Example A7

The siRNAs identified as described in Example A6 should function by a mechanism that includes being loaded in the RISC complex to cleave the cognate mRNA, leading to the degradation of the mRNA. To examine whether the siRNAs are effective in reducing the target mRNA, we used reverse transcription coupled with quantitative polymerase chain reaction (RT-qPCR) to assess the level of the target mRNA in HepG2.2.15 cells. All 32 siRNAs described in Table 2 reduced the mRNA by more than 75% (Table 3). A sampling of the percent reduction of the target mRNA by siRNAs is shown in FIG. 5B.

Example A7

The host factors likely function in viral infection as proteins. Therefore, we determined whether the siRNAs could decrease the amounts of the target protein. Cell transfected with 10 nM of each siRNA for 72 h were lysed and the target proteins identified using Western blots probed with target-specific antibodies. The effective siRNAs described in Table 3 reduced the levels of the proteins by between 28 and 92% of the mock-treated samples. The reduction in the proteins is less than the reduction of the target mRNA, likely due to the proteins have prolonged half-life and that more time is needed for their degradation. Examples of the reduction for RPLP1 and RPLP2 detected using Western blot analysis are shown in FIG. 5D. Notably, the knockdown of RPLP1 not only reduced the level of RPLP1, but also resulted in the decrease of RPLP2, and vice versa. We reason that this is due to RPLP1 and RPLP2 functioning as heterodimers such that a decrease of one protein increases the vulnerability of the other protein to degradation. Similar concomitant decrease of the proteins was reported by Campos et al. (17). Finally, the levels of two cellular proteins that are not targeted by the siRNAs, P54nrb and GAPDH, were unaffected. The results demonstrate that the siRNAs have specificity for their targets.

Example A8

The siRNAs listed in Table 2 were transfected into human colon epithelial HCT8 cells and the amount of OC43 virion produced was quantified. In these assays, the OC43 vRNA was quantified using a Branched DNA assay (QuantiGene gene expression assay: ThermoFisher). As a positive inhibitory control, the infected cells were treated with Remdesivir. Treatment with Remdesivir at 0.9 M resulted in more than 98% reduction in OC43 vRNA. In addition, siRNAs transfected into HCT8 cells at 10 nM final concentration resulted in a reduction of OC43 vRNA by between 36 and 94% (Table 3). Examples of the inhibition of OC43 vRNA are illustrated in FIG. 5A. These results confirm that the siRNAs that target host factors can inhibit human coronavirus infection.

Example A9

The host factors for HBV replication function in concert and knockdowns of multiple host factors resulted in more significant reductions in HBV replication and HBsAg production (FIG. 1B). A combination of siRNAs targeting the host factor should more robustly reduce OC43 virion production. To illustrate this, HCT8 cells were transfected with 10 nM of siRNAs from Table 2 along with 10 nM of siRNA targeting GRP78. The virion RNAs produced were quantified using the Branched DNA assay. The results show siRNAs that targeted GRP78 along with those that targeted SRSF1, RPLP1 or RPLP2 resulted in significant reductions of OC43 virion RNAs (Table 3). Examples of this activity are shown in FIG. 6B. A combination of siRNAs targeting host factors GRP78, SRSF1, RPLP1 and RPLP2 can lead to significant reduction in the production of human Coronavirus virion RNA from infected cells.

The results illustrated in Table 3 and FIGS. 1-6 demonstrate methods of reducing a level of a virus molecule produced by an infected cell by contacting the infected cell with an effective amount of an oligonucleotide inhibitor that targets the cellular host factor to thereby inhibit production by the infected cell of the cellular host factor and reduce the amount of the virus molecule produced by the infected cell. In some embodiments, the oligonucleotide inhibitors are siRNA having the structures represented by SEQ ID NOS 1-20. In other embodiments, the oligonucleotide inhibitors are siRNA having the structures represented by SEQ ID NOS 21-52 in Table 2.

REFERENCES CITED

1. Liang, T. J. 2009. Hepatitis B: The virus and disease. Hepatology 49: S13-S21.
2. Warfield K. L. 2019. Lack of selective resistance of influenza A virus in presence of targeted antiviral UV-4B. Scientific Report. 9:7484.
3. Li, W. 2015. The hepatitis B virus receptor. Annu. Rev. Cell Dev. Biol. 31: 125-47.
4. Ko C, Park W. J., Park S, Kim S, Windisch, M. P. and Ryu, W. S. 2015. The FDA approved drug irbesartan inhibits HBV infection in HepG2 cells stably expressing sodium taurocholate co-transporting polypeptide. Antivir. Ther. 20: 835-42.
5. Zhao R. et al. 2011. Hepatoma cell line HepG2.2.15 demonstrate distinct biological features compared with parental HepG2. World J. Gastroenterol. 17(9):1152-1159.
6. Mitra, B., Thapa, R. J., Guo H., and Block, T. M. 2018. Host functions used by hepatitis B virus to complete its life cycle: implications for developing host-targeting agents to treat chronic hepatitis B. Antiviral Res. 158: 185-98.
7. Shin, H. J., Kim, S. S., Cho, Y. H., Lee, S. G. and Rho, H. M. 2002. Host cell proteins binding to the encapsidation signal episilon in the hepatitis B virus RNA. Arch. Virol. 147: 471-91.
8. Pollack, J. and Ganem D. 1993. An RNA stem-loop structure directs hepatitis B virus genomic RNA encapsidation. J. Virol. 67: 3254-63.
9. Wang, M. et al. 2009. Role of the unfolded protein response regulator GRP78/BiP in development, cancer and neurological disorders. Antioxid. & Redox Signal. 11: 2307.
10. Li, Y. et al., 2019. Hepatitis B surface antigen activates unfolded protein response in forming ground glass hepatocytes of chronic hepatitis B. Viruses 11: 386.
11. Azarnez, I., et al. 2018. Mechanism of nonsense-mediated mRNA decay stimulation by splicing factor SRSF1. Cell Report 23: 2186-98.
12. Alacon C. R. et al. 2015. HNRNPA2B1 is a mediator of m6A-dependent nuclear RNA processing events. Cell 162: 1299-308.
13. Iman H. et al. 2018. N6-methyladenosine modification of the Hepatitis B virus RNA differentially regulates the viral life cycle., Proc. Natl. Acad. Sci. USA 115: 8829-34.

14. Wang, L., Wen, M., and Cao X. 2019. Nuclear HNRNPA2B1 initiates and amplifies the innate immune response to DNA viruses. Science: eaav0758.
15. Ballesta, J. P., Remacha, M. 1996. The large ribosomal stalk as a regulatory element of the eukaryotic translational machinery. Prog. Nucleic Acid Res. Mol Biol. 55: 157-193.
16. Choi. A. K. H. et al. 2015. Structures of eukaryotic ribosomal stalk proteins and their complex with trichosanthin and their implications in recruiting ribosome-inactivating proteins to the ribosomes. Toxins 7: 638.
17. Campos, R. K. et al. 2017. RPLP1 and RPLP2 are essential flavivirus host factors that promote early viral accumulation. J. Virol. 91: e01706-16.
18. Campos R. K. et al., 2019. Ribosomal stalk proteins RPLP1 and RPLP2 promote biogenesis of flaviviral and cellular multi-pass transmembrane proteins. BioRxiv. Doi 10.110/713016.
19. Kibbe W A. 2007 OligoCalc: an online oligonucleotide properties calculator. Nucl. Acids Res. 35 (webserver issue): May 25.
20. Coronaviridae Study Group of the International Committee on Taxonomy of Viruses. 2020. The species of Severe acute respiratory syndrome-related coronavirus: classifying the 2019-nCoV and naming it SARS-CoV2. Nature Microbiology 5, 536-544.
21. Wang M. Cao R., Zhang L., Yang X., Liu J. et al. 2020. Remdesivir and chloroquine effectively inhibits the recently emerged novel coronavirus (2019-nCoV) in vitro. Cell Research 30, 269-271.

What is claimed is:

1. A method of reducing a level of a hepatitis B virus (HBV) molecule produced by an infected cell, comprising:
   contacting the infected cell with an effective amount of an oligonucleotide inhibitor that targets a RPLP1 to thereby inhibit production of the RPLP1 by the infected cell and reduce the amount of the HBV virus molecule produced by the infected cell;
   wherein the infected cell produces an amount of at least one HBV molecule that the HBV utilizes for replication, wherein the HBV molecule is a viral protein, a viral DNA or a viral RNA.

2. The method of claim 1, wherein the cell is a mammalian cell.

3. The method of claim 2, wherein the mammalian cell is a human cell.

4. The method of claim 1, wherein the HBV molecule is an S-antigen, an E-antigen, a Core antigen, an HBV RNA, or an HBV DNA.

5. The method of claim 1, wherein the contacting of the infected cell with the effective amount of the oligonucleotide inhibitor reduces the amount of the HBV molecule produced by the infected cell by at least 20% as determined by an assay for the HBV molecule.

6. The method of claim 1, wherein the contacting of the infected cell with the effective amount of the oligonucleotide inhibitor reduces the amount of the HBV molecule produced by the infected cell by at least 30% as determined by an assay for the HBV molecule.

7. The method of claim 1, wherein the contacting of the infected cell with the effective amount of the oligonucleotide inhibitor reduces the amount of the HBV molecule produced by the infected cell by at least 40% as determined by an assay for the HBV molecule.

8. The method of claim 1, wherein the contacting of the infected cell with the effective amount of the oligonucleotide inhibitor reduces the amount of the HBV molecule produced by the infected cell by at least 50% as determined by an assay for the HBV molecule.

9. The method of claim 5, wherein the assay for the virus molecule is an HBV assay that quantitatively assesses HBsAg, HBeAg, HBV Core antigen, HBV RNA, or HBV DNA.

10. The method of claim 1, wherein the oligonucleotide inhibitor has an $EC_{50}$ value that is less than 100 nM as determined by the assay for the HBV molecule.

11. A method of treating an HBV infection, comprising:
    administering a therapeutically effective amount of an oligonucleotide inhibitor to a subject in need thereof, wherein the oligonucleotide inhibitor targets a RPLP1 to thereby reduce production of the RPLP1 by infected cells of the subject.

12. The method of claim 1, wherein the oligonucleotide inhibitor targets at least one of the RPLP1 RNA and the RPLP1 protein.

13. The method of claim 1, wherein the oligonucleotide inhibitor is an anti-sense oligonucleotide that specifically recognizes the target RNA, wherein the target RNA includes mRNA.

14. The method of claim 1, wherein the oligonucleotide inhibitor is a silencing RNA that specifically hybridizes to the target RNA, wherein the target RNA includes mRNA.

15. The method of claim 1, wherein the oligonucleotide inhibitor is an siRNA represented by a sequence of any one of SEQ ID NOS. 9-12, and 24-33.

16. The method of claim 1, wherein the oligonucleotide inhibitor comprises one or more chemically-modified nucleotides that enhance binding of the oligonucleotide inhibitor to the target RNA or target protein.

* * * * *